US005869464A

United States Patent [19]

Nomura et al.

[11] Patent Number: 5,869,464

[45] Date of Patent: Feb. 9, 1999

[54] 2'-DEOXY-5-FLUOROURIDINE DERIVATIVES, A PROCESS FOR THEIR PREPARATION, ANTITUMOR AGENTS CONTAINING SAME AND METHODS FOR USING SAID AGENTS

[75] Inventors: Makoto Nomura, Iruma; Makoto Kajitani, Hidaka; Junichi Yamashita, Honjo; Masakazu Fukushima; Yuji Shimamoto, both of Hanno, all of Japan

[73] Assignee: Taiho Pharmaceutical Co. Ltd., Tokyo, Japan

[21] Appl. No.: 505,291

[22] PCT Filed: Dec. 21, 1994

[86] PCT No.: PCT/JP94/02167

§ 371 Date: Aug. 21, 1995

§ 102(e) Date: Aug. 21, 1995

[87] PCT Pub. No.: WO95/18138

PCT Pub. Date: Jul. 6, 1995

[30] Foreign Application Priority Data

Dec. 24, 1993 [JP] Japan .................................... 5-327338

[51] Int. Cl.[6] ............................ A61K 31/70; C07H 19/06

[52] U.S. Cl. .............................. 514/50; 514/49; 514/908; 536/28.53; 536/28.54; 536/28.55

[58] Field of Search ............................. 536/28.53, 28.54, 536/28.55, 908; 514/49, 50, 908

[56] References Cited

U.S. PATENT DOCUMENTS

| | | |
|---|---|---|
| 4,605,645 | 8/1986 | Watanabe et al. . |
| 4,864,021 | 9/1989 | Fujii . |
| 4,946,951 | 8/1990 | Tada et al. . |
| 4,992,534 | 2/1991 | Fujii et al. . |

FOREIGN PATENT DOCUMENTS

| | | |
|---|---|---|
| 56-113797 | 9/1981 | Japan . |
| 57-28083 | 2/1982 | Japan . |
| 57-50999 | 3/1982 | Japan . |
| 57-109722 | 7/1982 | Japan . |
| 61-238797 | 10/1986 | Japan . |

OTHER PUBLICATIONS

Journal of Medicinal Chemistry, vol. 32, No. 1, Jan. 1989, Washington US, pp. 136–139.

Tetrahedron Letters, vol. 26, No. 40, 1985, Oxford GB, pp. 4915–4918.

Journal of Medicinal Chemistry, vol. 31, No. 2, 1988, Washington US, pp. 393–397.

*Primary Examiner*—James O. Wilson
*Attorney, Agent, or Firm*—Nikaido Marmelstein Murray & Oram, LLP

[57] ABSTRACT

The compounds of the invention are a 2'-deoxy-5-fluorouridine derivative represented by the formula

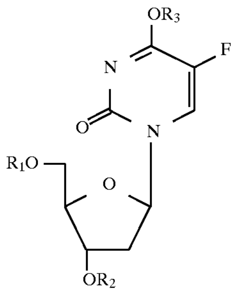

wherein one of $R_1$ and $R_2$ is a hydrogen atom or a group easily hydrolyzable in vivo, the other is a benzyl group which may optionally have at least one halogen atom or trifluoromethyl group as a substituent on the phenyl ring, and $R_3$ is a lower alkyl group, and a pharmaceutically acceptable salt thereof.

The compounds of the invention can be suitably used as an antitumor agent.

9 Claims, No Drawings

2'-DEOXY-5-FLUOROURIDINE DERIVATIVES, A PROCESS FOR THEIR PREPARATION, ANTITUMOR AGENTS CONTAINING SAME AND METHODS FOR USING SAID AGENTS

TECHNICAL FIELD

The present invention relates to novel 2'-deoxy-5-fluorouridine derivatives and pharmaceutically acceptable salts thereof. The compounds of the present invention have a high antitumor activity and are useful as an antitumor agent.

BACKGROUND ART

It is known that 240 -deoxy-5-fluorouridine (FdUrd) significantly inhibits the growth of tumor cells in in vitro tests. But when tested in vivo, FdUrd can not produce a satisfactory therapeutic effect under the influence of pyrimidine nucleoside phosphorylase acting as a decomposition enzyme. For this reason, FdUrd has not been widely used as a anti-cancer agent. Yet, FdUrd has been used for curing specific organic cancers although solely by a continuous administration method (Cancer 57 492–498 (1986), J. Urol. 139 259–262 (1988)). This suggests the possibility that FdUrd might be used as a clinically potent anti-cancer agent if the effective concentration of FdUrd in blood can be retained for a prolonged period. The production of various FdUrd derivatives has been attempted to improve said property (Japanese Unexamined Patent Publications Nos. 113797/1981, 109722/1982, 99499/1983 and 238797/1986). The compounds disclosed in the publications enable effective concentration of FdUrd in blood for a long period. But it was found that the compounds cause side effects such as diarrhea because of the increase of FdUrd concentration in blood beyond its effective concentration in blood, failing to produce a satisfactory clinical effect.

More recently, FdUrd derivatives were reportedly prepared with particular attention directed to the ability of FdUrd to sustain its low concentration in blood (Japanese Unexamined Patent Publications Nos. 106593/1986, 104093/1989 and 199992/1989). The compounds disclosed in the publications achieve an improvement in continuously releasing FdUrd into blood, but sustain the effective concentration of FdUrd in blood to a lesser extent than a continuous administration method because of a low conversion ratio from the compound to FdUrd, failing to give the desired therapeutic index.

DISCLOSURE OF THE INVENTION

The inventor of the present invention conducted extensive research to overcome the foregoing problems and discovered novel 2'-deoxy-5-fluorouridine derivatives having an excellent antitumor activity and a high therapeutic index, namely assuring a high safety. The present invention has been accomplished based on this novel finding.

According to the present invention, there is provided a 2'-deoxy-5-fluorouridine derivative represented by the formula (I)

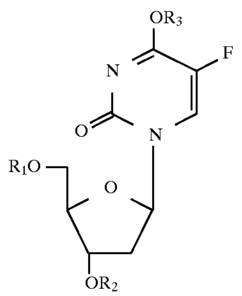

(I)

wherein one of $R_1$ and $R_2$ is a hydrogen atom or a group easily hydrolyzable in vivo, the other is a benzyl group which may optionally have at least one halogen atom or trifluoromethyl group as a substituent on the phenyl ring, and $R_3$ is a benzyl group which may optionally have at least one halogen atom as a substituent on the phenyl ring, a phenyl group, a lower alkenyl group or a lower alkyl group which may optionally have at least one substituent selected from the group consisting of a hydroxyl group, a lower alkoxy group, a di-lower alkylamino group, a furanyl group, a thienyl group and a pyridyl group, or a pharmaceutically acceptable salt thereof.

The compounds of the formula (I) according to the invention have a high antitumor activity and are effective in treating various tumors. The compounds of the invention have the advantages of sustaining a low FdUrd concentration in blood for an extended period, having a low toxicity and assuring a wide safety margin.

Consequently the present invention also provides an antitumor composition comprising an effective amount of the compound of the formula (I) or a pharmaceutically acceptable salt thereof and a pharmaceutically acceptable carrier.

Further, the present invention provides a method of treating mammals' tumors, comprising administering to a mammal the compound of the formula (I) or a pharmaceutically acceptable salt thereof.

Fluorine, chlorine, bromine and iodine can be mentioned as examples of halogen atoms which the benzyl groups represented by $R_1$, $R_2$ and $R_3$ in the formula (I) have as substituents on the phenyl ring. Among them, fluorine and chlorine are preferred. The number of halogen atoms as a substituent on the benzyl group is 1 to 5, preferably 1 to 3, more preferably 1 or 2. Examples of the benzyl group which may optionally have at least one halogen atom as a substituent on the phenyl ring are 2-fluorobenzyl, 3-fluorobenzyl, 4-fluorobenzyl, 2,3-difluorobenzyl, 2,4-difluorobenzyl, 2,4,6-trifluorobenzyl, 2-chlorobenzyl, 3-chlorobenzyl, 4-chlorobenzyl, 2,4-dichlorobenzyl, 3,4-dichlorobenzyl, 2-bromobenzyl, 3-bromobenzyl, 4-bromobenzyl, 2,4-dibromobenzyl, 3,4-dibromobenzyl, 4-chloro-2-fluorobenzyl, 2-chloro-4-fluorobenzyl, etc. Among them, preferred are 4-chlorobenzyl, 2,4-dichlorobenzyl, 4-chloro-2-fluorobenzyl and 2,4-difluorobenzyl.

Examples of the benzyl group represented by $R_1$ or $R_2$ and having at least one trifluoromethyl group on the phenyl ring are 2-trifluoromethylbenzyl, 3-trifluoromethylbenzyl and 4-trifluoromethylbenzyl. Among them, 4-trifluoromethylbenzyl is preferred.

Examples of the lower alkenyl group represented by $R_3$ are straight- or branched-chain alkenyl groups having 2 to 6 carbon atoms such as vinyl, 1-propenyl, isopropenyl, allyl, 2-butenyl, 2-methyl-2-butenyl, 3-pentenyl, 4-hexenyl, etc. Among them, vinyl, 1-propenyl and allyl are preferred and allyl is more preferred.

Examples of the lower alkyl group are straight- or branched-chain alkyl groups having 1 to 6 carbon atoms such as methyl, ethyl, n-propyl, isopropyl, n-butyl, sec-butyl, tert-butyl, pentyl, hexyl, etc. Among them, methyl, ethyl, n-propyl and n-butyl are preferred.

Examples of the lower alkoxy group are straight- or branched-chain alkoxy groups having 1 to 6 carbon atoms such as methoxy, ethoxy, n-propoxy, isopropoxy, n-butoxy, sec-butoxy, tert-butoxy, pentyloxy, hexyloxy, etc.

Examples of the di-lower alkylamino group are dialkylamino groups having 2 to 8 carbon atoms such as dimethylamino, diethylamino, dipropylamino, dibutylamino, etc.

Examples of the lower alkyl group having at least one hydroxyl group are straight- or branched-chain alkyl groups containing one or two hydroxyl groups and 1 to 6 carbon atoms such as hydroxymethyl, 1-hydroxyethyl, 2-hydroxyethyl, 2-hydroxypropyl, 3-hydroxypropyl, 2,3-dihydroxypropyl, 4-hydroxybutyl, 2,3-dihydroxybutyl, 5-hydroxypentyl, 6-hydroxyhexyl, etc. Among them, hydroxymethyl, 1-hydroxyethyl and 2-hydroxyethyl are preferred, and 2-hydroxyethyl is more preferred.

Examples of the lower alkyl group having at least one lower alkoxy group are alkoxyalkyl groups wherein each of the alkoxy moiety and alkyl moiety has 1 to 6 carbon atoms, such as methoxymethyl, ethoxymethyl, 2-methoxyethyl, 2-ethoxyethyl, 3-methoxypropyl, 4-ethoxybutyl, 6-propoxyhexyl, 5-isopropoxypentyl, 2-pentyloxyethyl, 2-hexyloxyethyl, etc. Preferred are methoxymethyl, ethoxymethyl and 2-methoxyethyl, and more preferred is 2-methoxyethyl.

Examples of the lower alkyl group having at least one di-lower alkylamino group are dialkylaminoalkyl groups wherein the alkyl moiety has 1 to 6 carbon atoms such as dimethylaminomethyl, dimethylaminoethyl, diethylaminomethyl, diethylaminoethyl, dipropylaminoethyl, dibutylaminoethyl, dibutylaminohexyl, etc. Preferred are dimethylaminoethyl, diethylaminoethyl and dipropylaminoethyl. More preferred is diethylaminoethyl.

The term "group easily hydrolyzable in vivo" used herein refers to a non-toxic group which is readily cleft in mammals's blood and tissue and then releases the compound of the formula (I) wherein one of groups represented by $R_1$ and $R_2$ is a hydrogen atom.

Examples of groups easily hydrolyzable in vivo include a wide range of acyl groups such as aliphatic acyl, aromatic acyl, etc. Specific examples include lower alkanoyl, arylcarbonyl, heterocyclic carbonyl, aryloxycarbonyl, lower alkoxycarbonyl, acyloxyacyl, etc.

Examples of the lower alkanoyl group are alkanoyl groups having 2 to 6 carbon atoms such as acetyl, propionyl, butyryl, isobutyryl, pentanoyl, hexanoyl, etc.

Examples of the arylcarbonyl group are benzoyl or naphthylcarbonyl groups optionally having lower alkyl group, lower alkoxy group, halogen atom, carboxyl group, nitro group, cyano group or the like as a substituent such as benzoyl, α-naphthylcarbonyl, β-naphthylcarbonyl, 2-methylbenzoyl, 3-methylbenzoyl, 4-methylbenzoyl, 2,4-dimethylbenzoyl, 4-ethylbenzoyl, 2-methoxybenzoyl, 3-methoxybenzoyl, 4-methoxybenzoyl, 2,4-dimethoxybenzoyl, 4-ethoxybenzoyl, 2-methoxy-4-ethoxybenzoyl, 2-chlorobenzoyl, 3-chlorobenzoyl, 4-chlorobenzoyl, 2,3-dichlorobenzoyl, 2-bromobenzoyl, 4-fluorobenzoyl, 2-carboxybenzoyl, 3-carboxybenzoyl, 4-carboxybenzoyl, 2-cyanobenzoyl, 4-cyanobenzoyl, 2-nitrobenzoyl, 4-nitrobenzoyl, 2,4-dinitrobenzoyl, etc.

Examples of the heterocyclic carbonyl group are 2-furanylcarbonyl, 4-thiazolylcarbonyl, 2-quinolylcarbonyl, 2-pyrazinylcarbonyl, 2-pyridylcarbonyl, 3-pyridylcarbonyl, 4-pyridylcarbonyl, etc.

Examples of the aryloxycarbonyl group are phenoxycarbonyl, α-naphthyloxycarbonyl, β-naphthyloxycarbonyl, 2-methylphenoxycarbonyl, 3-methylphenoxycarbonyl, 4-methylphenoxycarbonyl, 2,4-dimethylphenoxycarbonyl, 4-ethylphenoxycarbonyl, 2-methoxyphenoxycarbonyl, 3-methoxyphenoxycarbonyl, 4-methoxyphenoxycarbonyl, 2,4-dimethoxyphenoxycarbonyl, 4-ethoxyphenoxycarbonyl, 2-methoxy-4-ethoxyphenoxycarbonyl, 2-chlorophenoxycarbonyl, 3-chlorophenoxycarbonyl, 4-chlorophenoxycarbonyl, 2,3-dichlorophenoxycarbonyl, 2-bromophenoxycarbonyl, 4-fluorophenoxycarbonyl, β-methyl-α-naphthyloxycarbonyl, β-chloro-α-naphthyloxycarbonyl, etc.

Examples of the lower alkoxycarbonyl group are alkoxycarbonyl groups having 2 to 6 carbon atoms such as methoxycarbonyl, ethoxycarbonyl, propoxycarbonyl, isopropoxycarbonyl, butoxycarbonyl, pentyloxycarbonyl, etc.

Examples of the acyloxyacyl group are acetyloxyacetyl, propionyloxyacetyl, α-(acetyloxy)propionyl, β-(propionyloxy)propionyl, etc.

Of the groups easily hydrolyzable in vivo, preferred are lower alkanoyl group and arylcarbonyl group. More preferred are acetyl, benzoyl, 4-methylbenzoyl and 4-nitrobenzoyl.

Other groups easily hydrolyzable in vivo include groups conventionally used and disclosed, e.g. in Japanese Unexamined Patent Publications Nos. 106593/1986, 149696/1987 and 78350/1994, etc.

Preferred compounds of the invention are 2'-deoxy-5-fluorouridine derivatives of the formula (I) wherein $R_1$ is a hydrogen atom, a lower alkanoyl group or an arylcarbonyl group, $R_2$ is a benzyl group which has at least one halogen atom as a substituent on the phenyl ring, and $R_3$ is a benzyl group which has at least one halogen atom as a substituent on the phenyl ring, a phenyl group, a lower alkenyl group or a lower alkyl group optionally having at least one substituent selected from the group consisting of a hydroxyl group, a lower alkoxy group, a di-lower alkylamino group, a furanyl group, a thienyl group and a pyridyl group, and pharmaceutically acceptable salts thereof.

The most preferred compounds of the invention are 2'-deoxy-5-fluorouridine derivatives of the formula (I) wherein $R_1$ is a hydrogen atom, $R_2$ is a benzyl group which has one or two halogen atoms as substituents on the phenyl ring, and $R_3$ is a lower alkyl group and pharmaceutically acceptable salts thereof. Ethyl and n-propyl are preferred among the lower alkyl groups represented by $R_3$.

The 2'-deoxy-5-fluorouridine derivatives of the formula (I) according to the invention can be converted into an acid addition salt by causing a pharmaceutically acceptable acid to act on the derivative. Examples of such acids which can be used in the invention are inorganic acids such as hydrochloric acid, sulfuric acid, phosphoric acid, hydrobromic acid, nitric acid, etc., and organic acids such as oxalic acid, maleic acid, fumaric acid, malic acid, tartaric acid, citric acid, benzoic acid, 4-methylbenzenesulfonic acid, methanesulfonic acid, etc.

The present compounds of the formula (I) can be prepared according to the following reaction scheme.

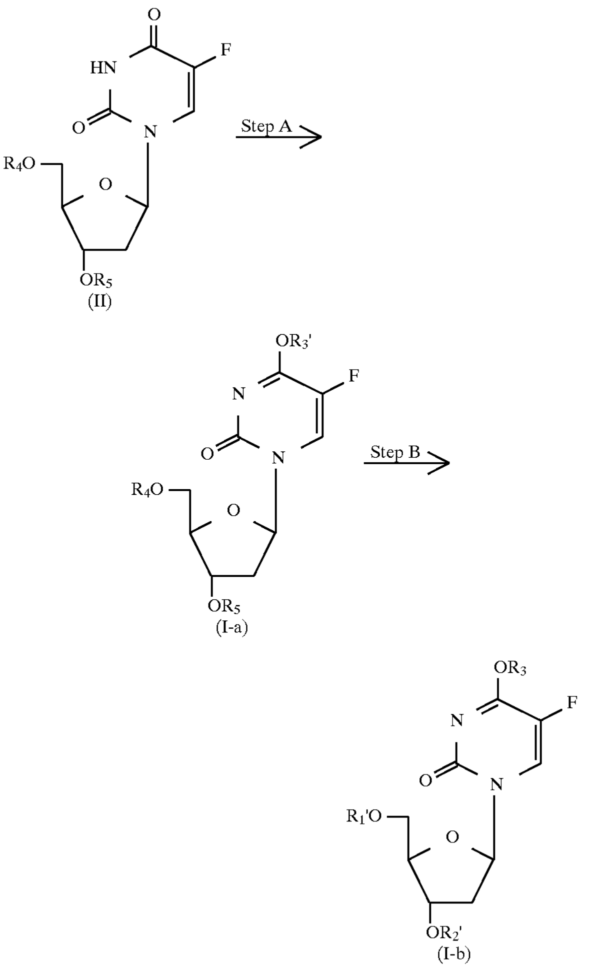

(II)
(I-a)
(I-b)

wherein $R_3$ are as defined above, one of $R_1$, and $R_2$, is a benzyl group which may optionally have at least one halogen atom or trifluoromethyl group as a substituent on the phenyl ring, the other is a hydrogen atom, one of $R_4$ and $R_5$ is a benzyl group which may optionally have at least one halogen atom or trifluoromethyl group as a substituent on the phenyl ring, the other is an acyl group, and $R_3$, is a benzyl group which may optionally have at least one halogen atom as a substituent on the phenyl ring, a phenyl group, a lower alkenyl group or a lower alkyl group optionally having at least one substituent selected from the group consisting of a hydroxyl group, a lower alkoxy group, a di-lower alkylamino group, a furanyl group, a thienyl group, a pyridyl group and a lower alkanoyl group.

The aforesaid benzyl groups can be exemplified as those which may optionally have at least one halogen atom or trifluoromethyl group as a substituent on the phenyl ring.

The acyl groups represented by $R_4$ and $R_5$ include, for example, the aforesaid aliphatic acyl, aromatic acyl and like acyl groups. Consequently the reaction may proceed using the compound having a group easily hydrolyzable in vivo. The acyl groups also include those conventionally used which are disclosed in Japanese Unexamined Patent Publications Nos. 106593/1986, 149696/1987 and 78350/1994, etc. Preferred acyl groups are acetyl, benzoyl, 4-methylbenzoyl, 4-nitrobenzoyl, etc.

The steps in the foregoing reaction scheme are described below in detail.

<Step A>

The known compound of the formula (II) which is described in Japanese Unexamined Patent Publication No. 106593/1986, etc. is reacted with a halogenating agent in a suitable organic solvent in the presence of a base. Subsequently a base is further added and the mixture is reacted with an alcohol represented by the formula $R_3$,OH wherein $R_3$, is as defined above, producing a compound represented by the formula (I-a).

Useful solvents are not specifically limited insofar as the solvent does not affect the reaction. Examples are halogenated hydrocarbons such as dichloromethane, chloroform, etc. and ethers such as tetrahydrofuran, dioxane, etc., aprotic solvents such as acetonitrile, etc.

Useful halogenating agents include a wide range of known reagents conventionally used for halogenation of hydroxyl groups. Examples are phosphorus pentachloride, phosphorus oxychloride, thionyl chloride, etc. Useful bases are selectable from a wide range of known bases and include 1-methylimidazole, triethylamine, pyridine, 4-dimethylaminopyridine, N-methylmorpholine and like organic amines.

The amounts of the above reagents used are not specifically limited. But it is preferred to use 3 to 60 moles of the base, 1 to 20 moles of the halogenating agent and 3 to 100 moles of the base to be further added and 2 to 500 moles of the alcohol of the formula $R_3$,OH, per mole of the compound of the formula (II). The reaction favorably proceeds if effected at a temperature of −100° to 100° C., preferably −20° to 40° C. for 10 minutes to 5 days, preferably 1 to 24 hours.

<Step B>

The compound of the formula (I-a) obtained in the step A is subjected to a reaction for the removal of acyl group in the presence of a base in an alcohol or in a mixture of an alcohol and an inert solvent, whereby the compound of formula (I-b) according to the present invention is produced.

Useful bases are not specifically limited and include, for example, trimethylamine, triethylamine and like organic amines, sodium carbonate, sodium hydroxide, potassium hydroxide and like inorganic bases, sodium methylate, sodium ethylate and like alcoholates, etc. Useful alcohols are, for example, methanol, ethanol, alcohol of the formula $R_3$,OH. Useful inert solvents are not specifically limited insofar as they do not affect the reaction. Examples of such solvents are dichloromethane, chloroform and like halogenated hydrocarbons, tetrahydrofuran, dioxane and like ethers, dimethylformamide, acetonitrile, etc.

The amount of the base used is not critical and is preferably in the range of from a catalytic amount to 50 moles per mole of the compound of the formula (I-a). The reaction favorably proceeds if effected at a temperature of −20° to 100° C., preferably −20° to 20° C. for 1 minute to 6 days, preferably 30 minutes to 3 days.

After execution of the step B, optionally the groups represented by $R_1$, and $R_2$, may be converted to groups easily hydrolyzable in vivo according to the acylation reaction described, e.g. in Japanese Unexamined Patent Publication No. 106593/1986.

When the base remains in the reaction mixture after completion of reaction for the removal of acyl group, the reaction mixture needs to be neutralized with a neutralizing agent. Useful neutralizing agents are not specifically limited and include, for example, organic acids such as formic acid, acetic acid, etc., inorganic acids such as hydrochloric acid, sulfuric acid, etc., tertiary amine salts such as triethylamine hydrochloride, silica gel, ion-exchange resin and so on. The neutralization may be conducted in the conventional manner.

The compounds obtained in the reactions can be isolated and purified by the procedures conventionally used, such as column chromatography, recrystallization, vacuum distillation, etc.

For use as a therapeutic drug for malignant tumors in mammals including humans, the compounds of the invention are provided in various pharmaceutical dosage forms according to therapeutic purposes. Examples of dosage forms are oral dosage forms such as tablets, coated tablets, pills, powders, granules, capsules, solutions, suspensions, emulsions, etc., parenteral dosage forms such as injections, suppositories, ointments, plasters, etc. Pharmaceutical preparations in these dosage forms can be manufactured by conventional pharmaceutical procedures known in the art.

As the carrier for shaping into the form of tablets, there can be employed various excipients such as lactose, sucrose, sodium chloride, glucose, urea, starch, calcium carbonate, kaolin, crystalline cellulose, silicic acid, etc.; binders such as simple syrup, glucose solution, starch solution, gelatin solution, carboxymethyl cellulose, shellac, methyl cellulose, potassium phosphate, polyvinyl pyrrolidone, etc.; disintegrators such as dry starch, sodium alginate, agar powder, laminaran powder, sodium hydrogencarbonate, calcium carbonate, polyoxyethylene sorbitan fatty acid esters, sodium lauryl sulfate, monoglyceride stearate, starch, lactose, etc.; antidisintegrators such as sucrose, stearic acid, cacao butter, hydrogenated oil, etc.; absorption promoters such as quaternary ammonium bases, sodium lauryl sulfate, etc.; humectants such as glycerol, starch, etc.; adsorbents such as starch, lactose, kaolin, bentonite, colloidal silicic acid, etc.; lubricants such as purified talc, stearic acid salt, boric acid powder, polyethylene glycol, etc. Where necessary, the tablets may be coated tablets such as sugar-coated tablets, gelatin-coated tablets, enteric-coated tablets, film-coated tablets, or double-layer or multi-layer tablets, etc.

The carrier for shaping into the form of pills includes, for example, various excipients such as glucose, lactose, starch, cacao butter, hardened vegetable oils, kaolin, talc, etc.; binders such as gum arabic powder, tragacanth powder, gelatin, etc.; and distintegrators such as laminaran, agar, etc.

The carrier for shaping into the form of suppositories includes, for example, polyethylene glycol, cacao butter, higher alcohols, esters of higher alcohols, gelatin, semi-synthetic glycerides, etc.

Capsules are manufactured in a usual manner by mixing the compound of the invention with any of the carriers mentioned above and encapsulating the mixture in hard gelatin or soft capsule or other capsules.

For use as injections, the solution, emulsion or suspension is preferably sterilized or rendered isotonic with blood. As diluents for use in the preparation of such dosage forms, water, ethyl alcohol, macrogols, propylene glycol, ethoxylated isostearyl alcohol, polyoxylated isostearyl alcohol, polyoxyethylene sorbitan fatty acid esters, etc. can be used. In this operation, sodium chloride, glucose or glycerin may be added and the conventional solubilizer, buffer and local anesthetic can also be added.

Ointments can be prepared in a usual manner by adding to the compound of the invention a base, stabilizer, humectant, preservative, etc. conventionally used in the art, where necessary. Examples of useful bases are liquid paraffin, white petrolatum, bleached beeswax, paraffin, etc. Useful preservatives are methyl para-hydroxy benzoate, ethyl para-hydroxy benzoate, propyl para-hydroxy benzoate, etc.

Plasters can be prepared in a usual manner by coating a usual support with said ointments, pastes, creams, gels, etc. Examples of useful supports include woven fabrics or nonwoven fabrics composed of cotton, rayon, chemical fibers or the like; films or foamed sheets made from soft polyvinyl chloride, polyethylene, polyurethane or the like; etc.

When required, the above preparations may contain coloring agents, preservatives, aroma enhancers, flavors, sweeteners, other medicaments, etc.

The amount of the compound of the invention to be incorporated in the pharmaceutical preparation is not specifically limited and can be selected from a wide range. A suitable amount is in the range of 1 to 70% by weight.

The mode of administration is not specifically limited and is suitably determined according to the dosage form, patients' age, sex and other factors, the degree of diseases, etc. For example, tablets, pills, solutions, suspensions, emulsions, granules and capsules are orally administered. Injections are intravenously administered alone or in mixture with conventional adjuvants such as glucose, amino acids, etc. or may be given intramascularly, intracutaneously, subcutaneously or intraperitoneally. Suppositories are applied directly into the rectum. Ointments are applied to the skin, mucous membrane in the mouth or the like.

The amount of the compound of the invention in any of the unit dosage forms depends on the clinical conditions of the patient to be treated and the particular dosage form selected. Generally, preferred amounts per dosage unit are about 1 to about 1,000 mg for oral preparations, about 0.1 to about 500 mg for injections, and about 5 to about 1,000 mg for suppositories. The daily dosage of any of the pharmaceutical preparations mentioned above is also dependent on the patients' condition, body weight, age, sex and other factors, but it is generally recommendable to administer about 0.1 to about 5,000 mg, preferably about 1 to about 1,000 mg, per day for an adult patient, either in a single dose or in 2 to 4 divided doses.

The malignant tumors to be treated with the pharmaceutical preparation containing the compound of the invention are not specifically limited and include, for example, cancers of the head and neck, esophagus, stomach, colon, rectum, liver, gallbladder-bile duct, pancreas, lung, breast, ovary, urinary bladder, prostate, testicles, uterine cervix, skin, brain and other parts, osteosarcoma or sarcoma of soft part, malignant lymphoma, leukemia, etc.

BEST MODE FOR CARRYING OUT THE INVENTION

Examples, Pharmacological Test Examples and Preparation Examples are presented below to clarify the present invention.

EXAMPLE 1

Synthesis of 3'-O-(4-chlorobenzyl)-2'-deoxy-4-O-ethyl-5-fluorouridine (compound 1)

A 15.9 ml quantity of 1-methylimidazole was dissolved in 108 ml of acetonitrile after which 5.6 ml of phosphorus oxychloride was added dropwise with stirring and ice-cooling. After stirring for 10 minutes, there was added 20 ml of an acetonitrile solution of 8.03 g of 5'-O-acetyl-3'-O-(4-chlorobenzyl)-2'-deoxy-5-fluorouridine prepared according to the process disclosed in Japanese Unexamined Patent Publication No. 106593/1986. The reaction mixture was warmed to room temperature and was stirred for 2 hours, followed by addition of 60 ml of ethanol. While the mixture was cooled to −20° C., 26.5 ml of triethylamine was added dropwise. After the reaction mixture was stirred for 24 hours at room temperature, the solvent was distilled off at reduced pressure. The residue was mixed with 150 ml of ethyl acetate after which the mixture was washed with water and with a saturated solution of sodium chloride and was dried over magnesium sulfate. After concentration, the concentrate was purified by silica gel column chromatography (eluate: n-hexane-ethyl acetate (1:1)), giving 6.4 g of 5'-O-acetyl-3'-O-(4-chlorobenzyl)-2'-deoxy-4-O-ethyl-5-fluorouridine in the form resembling a thick syrup (compound A: property values shown in Table 1).

The thick syrup-like substance (6.4 g) was dissolved in 85 ml of ethanol after which 15 ml of an ethanol solution of 200 mg of sodium ethylate was added at room temperature, followed by stirring overnight. After addition of silica gel to the reaction mixture, the solvent was distilled off and the residue was purified by silica gel column chromatography (eluate: chloroform-ethanol (25:1)), giving 3.4 g of the title compound (yield 70%).

Melting point: 105°–105.5° C.

$^1$H-NMR (DMSO-$d_6$) δ: 1.33 (3H, t, J=7.0 Hz), 2.06–2.17 (1H, m), 2.42–2.49 (1H, m), 3.60–3.67 (2H, m), 4.08–4.09 (1H, m), 4.14–4.20 (1H, m), 4.39 (2H, q, J=7.0 Hz), 4.53 (2H, s), 5.25 (1H, t, J=4.9 Hz, The peak disappeared by addition of $D_2O$), 6.08 (1H, t, J=5.9 Hz), 7.37 (2H, d, J=8.6 Hz), 7.43 (2H, d, J=8.6 Hz), 8.45 (1H, d, J=6.9 Hz)

EXAMPLES 2 and 3

Compounds 2 and 3 as shown below in Table 1 were prepared by the same procedure as in Example 1 with the exception of using 5'-O-acetyl-3'-O-(4-chloro-2-fluorobenzyl)-2'-deoxy-5-fluorouridine prepared according to the process disclosed in Japanese Unexamined Patent Publication No. 106593/1986 in place of the 5'-O-acetyl-3'-O-(4-chlorobenzyl)-2'-deoxy-5-fluorouridine used in Example 1 and using an alcohol and alcoholate having a substituent corresponding to the 4-position substituent of the contemplated compound.

EXAMPLE 4

Synthesis of 3'-O-(2,4-dichlorobenzyl)-2'-deoxy-4-O-methyl -5-fluorouridine (compound 4)

A 17.9 ml quantity of 1-methylimidazole was dissolved in 120 ml of acetonitrile after which 6.25 ml of phosphorus oxychloride was added dropwise with stirring and ice-cooling. To the mixture was added 10 g of 5'-O-acetyl-3'-O-(2,4-dichlorobenzyl)-2'-deoxy-5-fluorouridine prepared according to the process disclosed in Japanese Unexamined Patent Publication No. 106593/1986. The reaction mixture was warmed to room temperature and stirred for 2 hours, followed by addition of 52 ml of methanol. While the mixture was cooled to −20° C., 29.6 ml of triethylamine was added dropwise. After the solvent was distilled off at reduced pressure, the residue was mixed with 200 ml of ethyl acetate. The mixture was washed with water and with a saturated solution of sodium chloride and was dried over magnesium sulfate. After concentration, the concentrate was purified by silica gel column chromatography (eluate: dichloromethane-methanol (20:1)), giving 5.28 g of thick syrup-like 5'-O-acetyl-3'-O-(2,4-dichlorobenzyl)-2'-deoxy-4-O-methyl-5-fluorouridine (compound B: property values shown in Table 1).

The thick syrup-like substance (30 ml) was dissolved in 30 ml of methanol after which 7.7 ml of a methanol solution of 670 mg of sodium methylate was added at room temperature, followed by stirring for 4 hours. After the reaction mixture was neutralized with a strongly acidic ion-exchange resin (Dowex 50W, $H^+$ form, product of Dow Chemical Co.), the resin was filtered off and the filtrate was concentrated. The precipitated crystals were washed with water and dried at reduced pressure, giving 4.58 g of the title compound (yield 46%). The property values of the compound are shown in Table 1.

EXAMPLE 5

Compound 5 as shown below in Table 1 was prepared in the same manner as in Example 4 using 5'-O-acetyl-3'-O-(4-chlorobenzyl)-2'-deoxy-5-fluorouridine in place of 5'-O-acetyl -3'-O-(2,4-dichlorobenzyl)-2'-deoxy-5-fluorouridine used in Example 4, and using n-propanol and sodium n-propylate having a substituent corresponding to the 4 -position substituent of the contemplated compound.

EXAMPLE 6

Synthesis of 2'-deoxy-4-O-ethyl-3'-O-(2,4-difluorobenzyl)-5-fluorouridine (compound 6)

A 4.2 g quantity of 5'-O-acetyl-2'-deoxy-3'-O-(2,4-difluorobenzyl)-5-fluorouridine prepared according to the process disclosed in Japanese Unexamined Patent Publication No. 106593/1986 was dissolved in 50 ml of acetonitrile after which 8 ml of 1-methylimidazole was added. Then phosphorus oxychloride (2.9 ml) was added with ice-cooling. The mixture was stirred for 30 minutes at room temperature and 30 ml of ethanol was added. While the mixture was cooled to 0° C., 13. 2 ml of triethylamine was added dropwise. The reaction mixture was stirred at room temperature for 2 hours, and the solvent was distilled off. After addition of ethyl acetate to the residue, the mixture was washed with water and dried over magnesium sulfate. After concentration, the concentrate was purified by silica gel column chromatography (eluate: n-hexane-ethyl acetate (1:2)), giving 3.2 g of thick syrup-like 5'-O-acetyl-2'-deoxy-4-O-ethyl-3'-O-(2,4-difluorobenzyl)-5-fluorouridine (compound C: property values shown in Table 1).

The thick syrup-like substance was dissolved in 10 ml of ethanol, and 20 ml of an ethanol solution of 680 mg of sodium ethylate was added at room temperature, followed by stirring for 15 minutes. After neutralization of the reaction mixture with acetic acid, the solvent was distilled off. The residue was mixed with ethyl acetate after which the mixture was washed with water and dried over magnesium sulfate. The solvent was distilled off, giving 2.13 g of the title compound (yield 65%). The property values of the compound are shown in Table 1.

EXAMPLE 7

The procedure of Example 6 was repeated with the exception of using n-propanol and sodium n-propylate in place of the ethanol and sodium ethylate used in Example 6, giving compound 7 as shown in Table 1.

EXAMPLES 8 to 10

Compounds 8 to 10 as shown in Table 1 were prepared by the same procedure as in Example 6 with the exception of using 5'-O-acetyl-3'-O-(4-chlorobenzyl)-2'-deoxy-5-fluorouridine in place of 5'-O-acetyl-2'-deoxy-3'-O-(2,4-difluorobenzyl)-5-fluorouridine used in Example 6 and using an alcohol and alcoholate having a substituent corresponding to the 4-position substituent of the contemplated compound.

EXAMPLES 11 and 12

Compounds 11 and 12 as shown in Table 1 were prepared by the same procedure as in Example 6 with the exception of using 5'-O-acetyl-3'-O-(2,4-dichlorobenzyl)-2'-deoxy-5-fluorouridine in place of 5'-O-acetyl-2'-deoxy-3'-O-(2,4-difluorobenzyl)-5-fluorouridine used in Example 6 and using an alcohol and alcoholate having a substituent corresponding to the 4-position substituent of the contemplated compound.

EXAMPLE 13

Compound 13 as shown in Table 1 was prepared by the same procedure as in Example 6 with the exception of using 5'-O-acetyl-3'-O-(4-chloro-2-fluorobenzyl)-2'-deoxy-5-fluorouridine prepared according to the process disclosed in Japanese Unexamined Patent Publication No. 106593/1986 in place of 5'-O-acetyl-2'-deoxy-3'-O-(2,4-difluorobenzyl)-5-fluorouridine used in Example 6 and using an alcohol and alcoholate having a substituent corresponding to the 4-position substituent of the contemplated compound.

EXAMPLE 14

Synthesis of 3'-O-(4-chlorobenzyl)-2'-deoxy-4-O-(3-pyridylmethyl)-5-fluorouridine (compound 14)

A 12.8 ml quantity of 1-methylimidazole was dissolved in 40 ml of acetonitrile. Then 4.48 ml of phosphorus oxychloride was added dropwise with stirring and ice-cooling. After stirring for 10 minutes, 6.64 g of 5'-O-acetyl-3'-O-(4-chlorobenzyl)-2'-deoxy-5-fluorouridine was added. The reaction mixture was warmed to room temperature and stirred for 2 hours, followed by addition of 17.5 g of 3-pyridylmethanol. Then, 8 ml of triethylamine was added with ice-cooling. The reaction mixture was stirred at room temperature for 18 hours, and the solvent was distilled off at reduced pressure. The residue was mixed with 150 ml of ethyl acetate after which the mixture was washed with water and was dried over magnesium sulfate. The solvent was distilled off, giving 4.02 g of 5'-O-acetyl-3'-O-(4-chlorobenzyl)-2'-deoxy-4-O-(3-pyridylmethyl)-5-fluorouridine as a colorless powder (compound D: property values shown in Table 1).

A 3.78 g quantity of said powder was added to an alcoholate solution prepared by mixing sodium hydride with a solution of 3-pyridinemethanol in dimethylformamide. The mixture was stirred at room temperature for 45 minutes. A 2.2 g quantity of triethylamine hydrochloride was added and diethyl ether was added. The resulting mixture was washed with water and dried over magnesium sulfate. The solvent was distilled off and the residue was purified by silica gel column chromatography (eluate; dichloromethane-acetone (2:1)), giving 1.6 g of the title compound (yield 23%, based on compound D). The property values of the compound are shown in Table 1.

EXAMPLES 15 and 16

Compounds 15 and 16 as shown in Table 1 were prepared by the same procedure as in Example 14 with the exception of using an alcohol derivative having a substituent corresponding to the 4-position substituent of the contemplated compound in place of the 3-pyridinemethanol used in Example 14.

EXAMPLE 17

Synthesis of 3'-O-(4-chlorobenzyl)-2'-deoxy-4-O-methyl-5-fluorouridine (compound 17)

A 19.3 ml quantity of 1-methylimidazole was dissolved in 131 ml of acetonitrile after which 6.77 ml of phosphorus oxychloride was added dropwise with stirring and ice-cooling. A solution of 10 g of 5'-O-acetyl-3'-O-(4-chlorobenzyl)-2'-deoxy-5-fluorouridine in 28 ml of acetonitrile was added. The reaction mixture was warmed to room temperature and stirred for 3 hours, followed by addition of 54 ml of methanol. While the mixture was cooled to −20° C., 23.3 g of triethylamine was added dropwise. After the reaction mixture was stirred at room temperature for 24 hours, the solvent was distilled off at reduced pressure. The residue was mixed with 200 ml of ethyl acetate. Then the mixture was washed with water and a saturated aqueous solution of sodium chloride and dried over magnesium sulfate. The solvent was distilled off, giving 6.03 g of thick syrup-like 5'-O-acetyl-3'-O-(4-chlorobenzyl)-2'-deoxy-4-O-methyl-5-fluorouridine.

The thick syrup-like substance was dissolved in 30 ml of methanol. To the solution was added 11 ml of a methanol solution of 1.1 g of sodium methylate at room temperature. The mixture was stirred for 30 minutes. The crystals precipitated in the reaction mixture were collected by filtration, washed with water and dried, giving 4.3 g of the title compound (yield 46%). The property values of the compound are shown in Table 1.

EXAMPLE 18

Synthesis of 3'-O-(4-chlorobenzyl)-2'-deoxy-4-O-(2-thenyl)-5-fluorouridine (compound 18)

A 8.26 g quantity of 5'-O-acetyl-3'-O-(4-chlorobenzyl)-2'-deoxy-5-fluorouridine was dissolved in 100 ml of acetonitrile. Sixteen ml of 1-methylimidazole was added. After 5.72 ml of phosphorus oxychloride was added with ice-cooling, the mixture was stirred at room temperature for 30 minutes, and 18.9 ml of 2-thiophenemethanol was added. While the mixture was cooled to 0° C., 26.6 ml of triethylamine was added. After the reaction mixture was stirred at room temperature for 17 hours, the solvent was distilled off. The residue was mixed with 250 ml of ethyl acetate after which the mixture was washed with water and was dried over magnesium sulfate. After concentration, the concentrate was purified by silica gel column chromatography (eluate: n-hexane-ethyl acetate (1:2)), giving 4.18 g of thick syrup-like 5'-O-acetyl-3'-O-(4-chlorobenzyl)-2'-deoxy-4-O-(2-thenyl)-5-fluorouridine (compound E: property values of the compound shown in Table 1).

The thick syrup-like substance (1.8 g) was dissolved in a mixture of 0.6 ml of triethylamine, 6 ml of methanol and 3 ml of chloroform. The solution was stirred at room temperature for 3 days. The solvent was distilled off and the residue was purified by silica gel column chromatography (eluate: n-hexane-ethyl acetate (2:3)) and recrystallized from n-hexane-ethyl acetate, giving 1.06 g of the title compound (yield 62%, based on the compound E). The property values of the compound are shown in Table 1.

EXAMPLES 19 to 21

Compounds 19 to 21 as shown in Table 1 were prepared by the same procedure as in Example 18 with the exception of using an alcohol derivative having a substituent corresponding to the 4-position substituent of the contemplated compound in place of the 2-thiophenemethanol used in Example 18.

EXAMPLE 22

Synthesis of 3'-O-(4-chlorobenzyl)-2'-deoxy-4-O-(2-diethylaminoethyl)-5-fluorouridine (compound 22)

A 4.13 g quantity of 5'-O-acetyl-3'-O-(4-chlorobenzyl)-2'-deoxy-5-fluorouridine was dissolved in 50 ml of acetonitrile. Eight ml of 1-methylimidazole was added, followed by addition of 2.86 ml of phosphorus oxychloride with ice-cooling. After the mixture was stirred at room temperature for 30 minutes, 13.3 ml of 2-diethylaminoethanol was added. While the mixture was cooled to 0° C., 13.3 ml of triethylamine was added. After the reaction mixture was stirred at room temperature for 2.5 hours, the solvent was distilled off. The residue was mixed with 150 ml of ethyl acetate, and the mixture was washed with water and was dried over magnesium sulfate. After concentration, the concentrate was purified by silica gel column chromatography (eluate: chloroform-methanol (15:1)), giving 2.99 g of thick syrup-like 5'-O-acetyl-3'-O-(4-chlorobenzyl)-2'-deoxy-4-O-(2-diethylaminoethyl)-5-fluorouridine.

The thick syrup-like substance was dissolved in a mixture of 5 ml of methanol and 0.92 ml of triethylamine. The solution was stirred at room temperature for 27 hours. The solvent was distilled off and the residue was purified by silica gel column chromatography (eluate: chloroform-methanol (10:1)), giving 0.96 g of the title compound (yield 20%). The property values of the compound are shown in Table 1.

EXAMPLES 23 and 24

Compounds 23 and 24 as shown in Table 1 were prepared by the same procedure as in Example 22 with the exception of using an alcohol or phenol having a substituent corresponding to the 4-position substituent of the contemplated compound in place of the 2-diethylaminoethanol used in Example 22.

EXAMPLE 25

Synthesis of 3'-O-(4-chlorobenzyl)-2'-deoxy-4-O-(2-hydroxyethyl)-5-fluorouridine (compound 25)

A 4.13 g quantity of 5'-O-acetyl-3'-O-(4-chlorobenzyl)-2'-deoxy-5-fluorouridine was dissolved in 50 ml of acetonitrile after which 8 ml of 1-methylimidazole was added and 2.86 ml of phosphorus oxychloride was added with ice-cooling. After the solution was stirred at room temperature for 30 minutes, 12 ml of 2-acetoxyethanol was added. While the mixture was cooled to 0° C., 13.3 ml of triethylamine was added. After the reaction mixture was stirred at room temperature for 2 hours, the solvent was distilled off. The residue was mixed with 150 ml of ethyl acetate after which the mixture was washed with water and dried over magnesium sulfate. After concentration, the concentrate was purified by silica gel column chromatography (eluate: n-hexane-ethyl acetate (1:3)), giving 4.61 g of thick syrup-like 4-O-(2-acetoxyethyl)-5'-O-acetyl-3'-O-(4-chlorobenzyl)-2'-deoxy-5-fluorouridine (compound F: the property values of the compound shown in Table 1).

The thick syrup-like substance (3.9 g) was dissolved in a mixture of 10 ml of methanol and 1.2 ml of triethylamine. The solution was stirred at room temperature for 20 hours. The solvent was distilled off after which the residue was purified by silica gel column chromatography (eluate: chloroform-methanol (20:1)), giving 0.74 g of the title compound (yield 18%, based on compound F). The property values of the compound are shown in Table 1.

EXAMPLE 26

Synthesis of 2'-deoxy-3'-O-(2,4-difluorobenzyl)-4-O-methyl-5-fluorouridine (compound 26)

A 5 g quantity of 5'-O-acetyl-2'-deoxy-3'-O-(2,4-difluorobenzyl)-5-fluorouridine was dissolved in 80 ml of acetonitrile. To the solution was added 9.6 ml of 1-methylimidazole, followed by adding 3.4 ml of phosphorus oxychloride with ice-cooling. After stirring for 30 minutes at room temperature, 40 ml of methanol was added and 16 ml of triethylamine was added during cooling to 0° C. After the reaction mixture was stirred at room temperature for 20 minutes, the solvent was distilled off. The residue was mixed with 150 ml of ethyl acetate after which the mixture was washed with water and dried over magnesium sulfate. After concentration, the concentrate was purified by silica gel column chromatography (eluate: n-hexane-ethyl acetate (1:1)), giving 4.37 g of thick syrup-like 5'-O-acetyl-2'-deoxy-3'-O-(2,4-difluorobenzyl)-4-O-methyl-5-fluorouridine.

The thick syrup-like substance (4.35 g) was dissolved in 40 ml of methanol and 1.6 ml of triethylamine was added. The resulting mixture was stirred at room temperature for 16 hours. The solvent was distilled off, giving 3.37 g of the title compound as colorless powdery crystals (yield 67%, based on the thick syrup-like substance). The property values of the compound are shown in Table 1

EXAMPLE 27

Synthesis of 5'-O-(2,4-dichlorobenzyl)-2'-deoxy-4-O- ethyl-5-fluorouridine (compound 17)

A 2.24 g quantity of 3'-O-acetyl-5'-O-(2,4-dichlorobenzyl)-2'-deoxy-5-fluorouridine was dissolved in 35 ml of acetonitrile. Subsequently 4 ml of 1-methylimidazole was added, followed by adding 1.4 ml of phosphorus oxychloride with ice-cooling. After stirring for 1.5 hours at room temperature, 17.6 ml of ethanol was added and 6.95 ml of triethylamine was added dropwise during cooling to 0° C. After the reaction mixture was stirred at room temperature for 1.5 hours, the solvent was distilled off. The residue was mixed with ethyl acetate after which the mixture was washed with water and dried over magnesium sulfate. Concentration gave 3 g of an oil containing 3'-O-acetyl-5'-O-(2,4-dichlorobenzyl)-2'-deoxy-4-O-ethyl-5-fluorouridine. The oil was dissolved in 30 ml of ethanol. To the solution was added 72 mg of sodium ethylate, followed by stirring for 45 minutes with ice-cooling. The reaction mixture was neutralized with 0.1 ml of acetic acid and the solvent was distilled off. After addition of ethyl acetate to the residue, the mixture was washed with water and dried over magnesium sulfphate. The solvent was distilled off, giving 1.32 g of the title compound (yield 61%). The property values of the compound are shown in Table 1.

EXAMPLE 28

Synthesis of 2'-deoxy-4-O-methyl-3'-O-(4-trifluoromethylbenzyl)-5-fluorouridine (compound 28)

A 6.71 ml quantity of 1-methylimidazole was dissolved in 45 ml of acetonitrile. Thereafter 2.35 ml of phosphorus oxychloride was added dropwise with ice-cooling and stirring. After stirring for 10 minutes, there was added 10 ml of a solution of 3.65 g of 5'-O-acetyl-2'-deoxy-3'-O-(4-trifluoromethylbenzyl)-5-fluorouridine prepared according to the process disclosed in Japanese Unexamined Patent Publication No. 106593/1986 in acetonitrile. The reaction mixture was warmed to room temperature and stirred for 2 hours, followed by addition of 31.2 ml of methanol. Then, 26.5 ml of triethylamine was added dropwise with ice-cooling and the reaction mixture was stirred at room temperature for 19 hours. Thereafter the solvent was distilled off at reduced pressure. After the residue was mixed with ethyl acetate, the mixture was washed with water and a saturated aqueous solution of sodium chloride and was dried over magnesium sulfate. After concentration, the concentrate was purified by silica gel column chromatography (eluate: n-hexane-ethyl acetate (1:2)), giving 2.8 g of thick syrup-like 5'-O-acetyl-2'-deoxy-4-O-methyl-3'-O-(4-trifluoromethylbenzyl)-5-fluorouridine (compound G: the property values of the compound are shown in Table 1).

The thick syrup-like substance (2.8 g) was dissolved in 20 ml of methanol and 1.0 ml of triethylamine was added. The solution was stirred at room temperature for 45 hours. The solvent was distilled off, giving 2.38 g of the title compound as a colorless powder (yield 70%). The property values of the compound are shown in Table 1.

EXAMPLE 29

Synthesis of 5'-O-(benzoyl-3'-O-(4-chloro-2-fluorobenzyl)-2'-deoxy-4-O-ethyl-5-fluorouridine (compound H)

A 3.0 g quantity of 5'-O-benzoyl-3'-O-(4-chloro-2-fluorobenzyl)-2'-deoxy-5-fluorouridine prepared according to the process disclosed in Japanese Unexamined Patent Publication No. 106593/1986 was dissolved in 36 ml of acetonitrile. Then 4.88 ml of 1-methylimidazole was added and 1.73 ml of phosphorus oxychloride was added with ice-cooling, followed by 1 hours of stirring at room temperature. Ethanol (4.8 ml) was added and 6.8 ml of triethylamine was added with ice-cooling, followed by 13 hours of stirring at room temperature. The precipitated insolubles were filtered off and the solvent was distilled off from the filtrate at reduced pressure. The residue was dissolved in ethyl acetate, washed with water three times, and dried over magnesium sulfate. The solvent was distilled off at reduced pressure. The residue was purified by silica gel column chromatography (eluate: n-hexane-ethyl acetate (1:1)), giving 2.5 g of the title compound (yield 81%) in a thick syrup-like form. The property values of the compound are shown in Table 1.

EXAMPLE 30

Synthesis of 3'-O-(4-chloro-2-fluorobenzyl)-2'-deoxy-4-O-ethyl-5'-O-(4-nitrobenzoyl)-5-fluorouridine (compound I)

A 5.38 g quantity of 3'-O-(4-chloro-2-fluorobenzyl)-2'-deoxy-5'-O-(4-nitrobenzoyl)-5-fluorouridine prepared according to the process disclosed in Japanese Unexamined Patent Publication No. 106593/1986 was suspended in 80 ml of acetonitrile. Then 7.97 ml of 1-methylimidazole was added and 2.80 ml of phosphorus oxychloride was added with ice-cooling, followed by 1 hours of stirring at room temperature. Ethanol (35 ml) and 13.9 ml of triethylamine were added. The reaction mixture was stirred at room temperature for 1.5 hours. The precipitated insolubles were filtered off after which the solvent was distilled off from the filtrate at reduced pressure. After the residue was dissolved in ethyl acetate, the solution was washed with water and a saturated aqueous solution of sodium chloride, and dried over magnesium sulfate. The solvent was distilled off at reduced pressure and the residue was evaporated to dryness. The residue was dissolved in a small amount of ethyl acetate and n-hexane was added in small amounts. The precipitated crystals were separated by filtration and dried at reduced pressure, giving 3.76 g of the title compound (yield 66%). The property values of the compound are shown in Table 1.

EXAMPLE 31

Synthesis of 3'-O-(4-chloro-2-fluorobenzyl)-2'-deoxy-4-O-ethyl-5'-O-(4-methylbenzoyl)-5-fluorouridine (compound J)

A 3.0 g quantity of 3'-O-(4-chloro-2-fluorobenzyl)-2'-deoxy-5'-O-(4-methylbenzoyl)-5-fluorouridine prepared according to the process disclosed in Japanese Unexamined Patent Publication No. 106593/1986 was suspended in 35 ml of acetonitrile. Then 4.74 ml of 1-methylimidazole was added. After 1.68 ml of phosphorus oxychloride was added with ice-cooling, the mixture was stirred at room temperature for 1 hour. Ethanol (4.67 ml) was added, followed by addition of 6.61 ml of triethylamine with ice-cooling. The reaction mixture was stirred at room temperature for 7 hours. The precipitated insolubles were filtered off and the solvent was distilled off from the filtrate at reduced pressure. The residue was dissolved in 300 ml of ethyl acetate. The solution was washed with water three times and dried over magnesium sulfate. The solvent was distilled off at reduced pressure. The residue was purified by silica gel column chromatography (eluate: n-hexane-ethyl acetate (1:2)), giving 2.6 g of the title compound as a thick syrup-like substance (yield 82%). The property values of the compound are shown in Table 1.

EXAMPLE 32

Synthesis of 5'-O-acetyl-3'-O-(4-chlorobenzyl)-2'-deoxy-4-O-ethyl-5-fluorouridine (compound A)

A 399 mg quantity of 3'-O-(4-chlorobenzyl)-2'-deoxy-4-O-ethyl-5-fluorouridine prepared in Example 1 was dissolved in 1.3 ml of acetonitrile. To the solution were added 10 mg of 4-dimethylaminopyridine and 0.16 ml of triethylamine. Then 1.10 ml of acetic anhydride was added after which the mixture was stirred at room temperature for 1 hour. The reaction mixture was concentrated at reduced pressure and the residue was purified by silica gel column chromatography (eluate: chloroform-ethanol (20:1)), giving 406 mg of the title compound as a thick syrup-like substance (yield 92%).

EXAMPLE 33

Synthesis of 3'-O-(4-chloro-2-fluorobenzyl)-2'-deoxy-4-O-ethyl-5'-O-(4-nitrobenzoyl)-5-fluorouridine (compound I)

A 833 mg quantity of 3'-O-(4-chloro-2-fluorobenzyl)-2'-deoxy-4-O-ethyl-5-fluorouridine prepared in Example 13 was dissolved in 2.5 ml of acetonitrile. Then 15 mg of 4-dimethylaminopyridine and 0.307 ml of triethylamine were added. After addition of 408 mg of p-nitrobenzoyl chloride, the mixture was stirred at room temperature for 1 hour. The precipitate was filtered off and the filtrate was concentrated at reduced pressure. After the residue was dissolved in ethyl acetate, the solution was washed with water and dried over magnesium sulfate. The solvent was distilled off, and the residue was purified by silica gel column chromatography (eluate: chloroform-ethanol (20:1) ), and crystallized from ethanol, giving 775 mg of the title compound (yield 69%).

TABLE 1

Compound 1

$R_1$ = H $R_2$ = 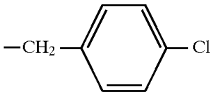

$R_3$ = $-CH_2CH_3$
Yield: 70%
Crystal form: Colorless powder
Meltingn point: 105–105.5° C.
$^1$H-NMR(DMSO-$d_6$)δ:
8.45(1H, d, J=6.9Hz), 7.43(2H, d, J=8.6Hz), 7.37(2H, d, J=8.6Hz), 6.08(1H, t, J=5.9Hz), 5.25(1H, t, J=4.9Hz, $D_2O$*1), 4.53(2H, s), 4.39(2H, q, J=7.0Hz), 4.14–4.20(1H, m), 4.08–4.09 (1H, m), 3.60–3.67(2H, m), 2.42–2.49(1H, m), 2.06–2.17(1H, m), 1.33(3H, t, J=7.0Hz)

Compound 2

$R_1$ = H $R_2$ = 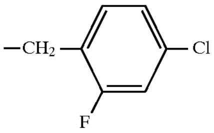

$R_3$ = $-CH_3$
Yield: 58%
Crystal form: Colorless powder
Melting point: 114–114.5° C.
$^1$H-NMR(DMSO-$d_6$)δ:
8.45(1H, d, J=6.6Hz), 7.51(1H, t, J=8.2Hz), 7.44(1H, dd, J=10.1 Hz, 1.9Hz), 7.31(1H, dd, J=8.2Hz, 1.9Hz), 6.08(1H, t, J=5.7Hz), 5.26(1H, t, J=5.1Hz, $D_2O$*1), 4.57(2H, s), 4.18–4.24(1H, m), 4.06–4.10(1H, m), 3.92(3H, s), 3.57–3.70(2H, m), 2.4–2.49(1H, m), 2.1–2.4(1H, m)

Compound 3

$R_1$ = H $R_2$ = 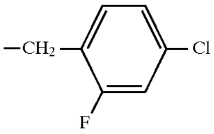

$R_3$ = $-CH_2CH_2CH_3$
Yield: 66%
Crystal form: Colorless powder
Melting point: 112–113° C.
$^1$H-NMR(DMSO-$d_6$)δ:
8.45(1H, d, J=6.6Hz), 7.51(1H, t, J=8.2Hz), 7.44(1H, dd, J=10.1Hz, 2.0Hz), 7.31(1H, dd, J=8.2Hz, 2.0Hz), 6.07(1H, t, J=5.6Hz), 5.26(1H, t, J=5.0Hz, $D_2O$*1), 4.57(2H, s), 4.30(2H, t, J=6.6Hz), 4.19–4.22(1H, m), 4.07–4.08(1H, m), 3.60–3.67 (2H, m), 2.39–2.47(1H, m), 2.1–2.20(1H, m), 1.70–1.78(2H, m), 0.95(3H, t, J=7.3Hz)

Compound 4

$R_1$ = H $R_2$ = 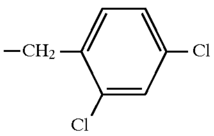

$R_3$ = $-CH_3$
Yield: 46%
Crystal form: Colorless powder
Melting point: 78–81° C.
$^1$H-NMR(DMSO-$d_6$)δ:

TABLE 1-continued 8.46(1H, d, J=6.6Hz), 7.64(1H, d, J=2.0Hz), 7.55(1H, d, J=8.3Hz), 7.46(1H, dd, J=8.3Hz, 2.0Hz), 6.10(1H, t, J=5.6Hz), 5.28(1H, t, J=5.0Hz, $D_2O$*1), 4.59(2H, s), 4.22–4.27(1H, m), 4.09–4.12(1H, m), 3.93(3H, s), 3.62–3.68(2H, m), 2.43–2.51 (1H, m), 2.14–2.18(1H, m)

Compound 5

$R_1$ = H $R_2$ = 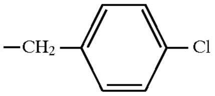

$R_3$ = $-CH_2CH_2CH_3$
Yield: 64%
Crystal form: Colorless powder
Melting point: 126.5–127.5° C.
$^1$H-NMR(DMSO-$d_6$)δ:
8.45(1H, d, J=6.6Hz), 7.42(2H, d, J=8.6Hz), 7.37(2H, d, J=8.6Hz), 6.08(1H, t, J=5.8Hz), 5.26(1H, t, J=5.0Hz, $D_2O$*1), 4.53(2H, s), 4.30(2H, t, J=6.6Hz), 4.16–4.20(1H, m), 4.08–4.11 (1H, m), 3.60–3.67(2H, m), 2.40–2.50(1H, m), 2.10–2.18(1H, m), 1.69–1.78(2H, m), 0.95(3H, t, J=7.4Hz)

Compound 6

$R_1$ = H $R_2$ = 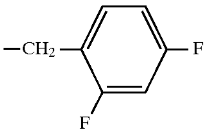

$R_3$ = $-CH_2CH_3$
Yield: 65%
Crystal form: Colorless powder
Melting point: 75–76° C.
$^1$H-NMR(DMSO-$d_6$)δ:
8.45(1H, d, J=6.6Hz), 7.52(1H, q, J=8.0Hz), 7.06–7.29(2H, m), 6.07(1H, t, J=5.8Hz), 5.26(1H, t, J=5.0Hz, $D_2O$*1), 4.55(2H, s), 4.39(2H, q, J=7.1Hz), 4.18–4.22(1H, m), 4.06–4.09 (1H, m), 3.57–3.70(2H, m), 2.38–2.51(1H, m), 2.09–2.19(1H, m), 1.33(3H, t, J=7.1Hz)

Compound 7

$R_1$ = H $R_2$ = 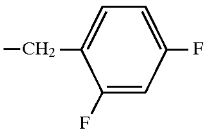

$R_3$ = $-CH_2CH_2CH_3$
Yield: 72%
Crystal form: Colorless powder
Melting point: 97–98° C.
$^1$H-NMR(DMSO-$d_6$)δ:
8.45(1H, d, J=6.6Hz), 7.1–7.6(3H, m), 6.07(1H, t, J=5.8Hz), 5.26(1H, t, J=5.0Hz, $D_2O$*1), 4.55(2H, s), 4.30(2H, t, J=6.8Hz), 4.18–4.22(1H, m), 4.06–4.09(1H, m), 3.55–3.69(2H, m), 2.38–2.49(1H, m), 2.09–2.20(1H, m), 1.67–1.80(2H, m), 0.94(3H, t, J=7.3Hz)

Compound 8

$R_1$ = H $R_2$ = 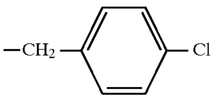

$R_3$ = $-CH_2(CH_2)_2CH_3$
Yield: 69%
Crystal form: Colorless powder

TABLE 1-continued

Melting point: 103–104° C.
$^1$H-NMR(DMSO-$d_6$)δ:
8.45(1H, d, J=6.6Hz), 7.43(2H, d, J=8.6Hz), 7.37(2H, d, J=8.6Hz), 6.08(1H, t, J=5.9Hz), 5.26(1H, t, J=4.9Hz, $D_2O$*1), 4.53(2H, s), 4.34(2H, t, J=6.6Hz), 4.16–4.20(1H, m), 4.03–4.09 (1H, m), 3.59–3.66(2H, m), 2.38–2.47(1H, m), 2.06–2.19(1H, m), 1.67–1.73(2H, m), 1.35–1.43(2H, m), 0.92(3H, t, J=7.6Hz)

Compound 9

$R_1$ = H $R_2$ = 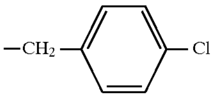

$R_3$ = $-CH_2CH{=}CH_2$
Yield: 82%
Crystal form: Colorless powder
Melting point: 124–125° C.
$^1$H-NMR(DMSO-$d_6$)δ:
8.48(1H, d, J=6.6Hz), 7.43(2H, d, J=8.6Hz), 7.37(2H, d, J=8.6Hz), 6.00–6.10(2H, m), 5.29–5.45(2H, m), 5.26(1H, t, J=4.9Hz, $D_2O$*1), 4.88(2H, d, J=5.6Hz), 4.53(2H, s), 4.18–4.20(1H, m), 4.09–4.10(1H, m), 3.62–3.66(2H, m), 2.44–2.49(1H, m), 2.14–2.16(1H, m)

Compound 10

$R_1$ = H $R_2$ = 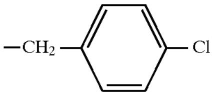

$R_3$ = $-CH_2CH_2OCH_3$
Yield: 57%
Crystal form: Colorless powder
Melting point: 73–74° C.
$^1$H-NMR(DMSO-$d_6$)δ:
8.47(1H, d, J=6.6Hz), 7.42(2H, d, J=8.9Hz), 7.37(2H, d, J=8.9Hz), 6.08(1H, t, J=5.9Hz), 5.27(1H, t, J=5.0Hz, $D_2O$*1), 4.53(2H, s), 4.46(2H, m), 4.16–4.18(1H, m), 4.09–4.11(1H, m), 3.60–3.68(4H, m), 3.29(3H, s), 2.13–2.16(1H, m), 2.41–2.49(1H, m)

Compound 11

$R_1$ = H $R_2$ = 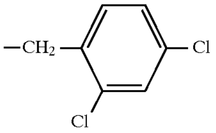

$R_3$ = $-CH_2CH_3$
Yield: 67%
Crystal form: Colorless powder
Melting point: 119.5–120.5° C.
$^1$H-NMR(DMSO-$d_6$)δ:
8.46(1H, d, J=6.6Hz), 7.63(1H, d, J=2.0Hz), 7.55(1H, d, J=8.3Hz), 7.46(1H, dd, J=8.3Hz, 2.0Hz), 6.10(1H, t, J=5.6Hz), 5.28(1H, br, $D_2O$*1), 4.59(2H, s), 4.39(2H, q, J=7.1Hz), 4.23–4.26(1H, m), 4.10–4.11(1H, m), 3.64–3.67(2H, m), 2.45–2.51(1H, m), 2.16–2.20(1H, m), 1.33(3H, t, J=7.1Hz)

Compound 12

$R_1$ = H $R_2$ = 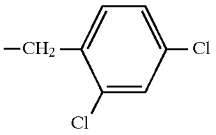

$R_3$ = $-CH_2CH_2CH_3$
Yield: 67%
Crystal form: Colorless powder
Melting point: 120–121° C.
$^1$H-NMR(DMSO-$d_6$)δ:
8.46(1H, d, J=6.6Hz), 7.63(1H, d, J=2.0Hz), 7.54(1H, d, J=8.3Hz), 7.46(1H, dd, J=8.3Hz, 2.0Hz), 6.09(1H, t, J=7.1Hz), 5.28(1H, t, J=5.0Hz, $D_2O$*1), 4.59(2H, s), 4.30(2H, t, J=6.6Hz), 4.22–4.26(1H, m), 4.08–4.12(1H, m), 3.62–3.68(2H, m), 2.43–2.52 (1H, m), 2.14–2.22(1H, m), 1.70–1.78(2H, m), 0.95(3H, t, J=7.4Hz)

Compound 13

$R_1$ = H $R_2$ = 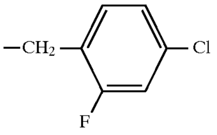

$R_3$ = $-CH_2CH_3$
Yield: 73%
Crystal form: Colorless powder
Melting point: 103–103.5° C.
$^1$H-NMR(DMSO-$d_6$)δ:
8.45(1H, d, J=6.9Hz), 7.51(1H, t, J=8.2Hz), 7.47(1H, dd, J=10.Hz, 2.0Hz), 7.32(1H, dd, J=8.2Hz, 2.0Hz), 6.07(1H, t, J=5.8Hz), 5.27(1H, t, J=5.1Hz, $D_2O$*1), 4.57(2H, s), 4.39(2H, q, J=7.1Hz), 4.19–4.22(1H, m), 4.07–4.10(1H, m), 3.57–3.68(2H, m), 2.39–2.51(1H, m), 2.10–2.20(1H, m), 1.33(3H, t, J=7.1Hz)

Compound 14

$R_1$ = H $R_2$ = 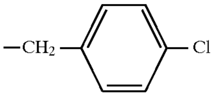

$R_3$ = 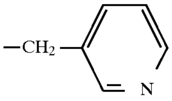

Yield: 23%
Crystal form: Colorless powder
Melting point: 113–114° C.
$^1$H-NMR(DMSO-$d_6$)δ:
8.69(1H, d, J=1.6Hz), 8.58(1H, dd, J=4.4Hz, 1.6Hz), 8.50(1H, d, J=6.6Hz), 7.90(1H, dt, J=8.3Hz, 1.6Hz), 7.35–7.47(5H, m), 6.09(1H, t, J=5.6Hz), 5.47(2H, s), 5.26(1H, t, J=5.0Hz, $D_2O$*1), 4.54(2H, s), 4.17–4.21(1H, m), 4.08–4.12(1H, m), 3.57–3.72(2H, m), 2.42–2.51(1H, m), 2.09–2.19(1H, m)

Compound 15

$R_1$ = H $R_2$ = 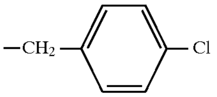

$R_3$ = 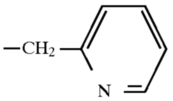

Yield: 33%
Crystal form: Colorless powder
Melting point: 134–137° C.
$^1$H-NMR(DMSO-$d_6$)δ:
8.59(1H, d, J=3.6Hz), 8.53(1H, d, J=6.6Hz), 7.82–7.89(1H, m), 7.35–7.51(6H, m), 6.09(1H, t, J=5.8Hz), 5.49(2H, s), 5.27(1H, t, J=5.1Hz, $D_2O$*1), 4.54(2H, s), 4.17–4.20(1H, m), 4.10–4.11(1H, m), 3.57–3.73(2H, m), 2.42–2.51(1H, m), 2.09–2.20(1H, m)

TABLE 1-continued

Compound 16

$R_1$ = H $R_2$ = 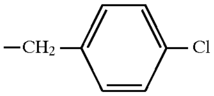

$R_3$ = 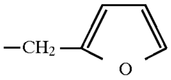

Yield: 5%
Crystal form: Colorless powder
Melting point: 121–122° C.
$^1$H-NMR(DMSO-$d_6$)δ:
8.32(1H, d, J=6.9Hz), 7.56(1H, d, J=2.0Hz), 7.43(2H, d, J=8.6Hz), 7.37(2H, d, J=8.6Hz), 6.39(1H, dd, J=2.0Hz, 3.3Hz), 6.33(1H, d, J=3.3Hz), 6.18(1H, t, J=5.8Hz), 5.26(1H, t, J=4.9Hz, $D_2O$*1), 4.98(2H, s), 4.53(2H, s), 4.18–4.20(1H, m), 4.05–4.06(1H, m), 3.59–3.63(2H, m), 2.37–2.49(1H, m), 2.20–2.23(1H, m)

Compound 17

$R_1$ = H $R_2$ = 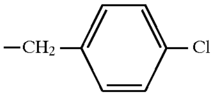

$R_3$ = $-CH_3$
Yield: 46%
Crystal form: Colorless powder
Melting point: 143–144° C.
$^1$H-NMR(DMSO-$d_6$)δ:
8.46(1H, d, J=6.6Hz), 7.42(2H, d, J=8.6Hz), 7.37(2H, d, J=8.6Hz), 6.09(1H, t, J=5.6Hz), 5.25(1H, t, J=5.1Hz, $D_2O$*1), 4.53(2H, s), 4.16–4.20(1H, m), 4.07–4.11(1H, m), 3.92(3H, s), 3.60–3.68(2H, m), 2.40–2.49(1H, m), 2.10–2.18(1H, m)

Compound 18

$R_1$ = H $R_2$ = 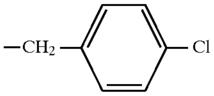

$R_3$ = 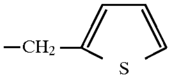

Yield: 62%
Crystal form: Colorless powder
Melting point: 119–120° C.
$^1$H-NMR(DMSO-$d_6$)δ:
8.50(1H, d, J=6.6Hz), 7.62(1H, d, J=5.1Hz), 7.42(2H, d, J=8.9Hz), 7.37(2H, d, J=8.9Hz), 7.04–7.30(2H, m), 6.10(1H, t, J=5.9Hz), 5.61(2H, s), 5.26(1H, t, J=5.0Hz, $D_2O$*1), 4.54(2H, s), 4.18–4.20(1H, m), 4.09–4.10(1H, m), 3.60–3.67 (2H, m), 2.43–2.49(1H, m), 2.15–2.17(1H, m)

Compound 19

$R_1$ = H $R_2$ = 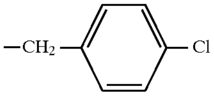

$R_3$ = 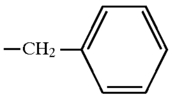

TABLE 1-continued

Yield: 67%
Crystal form: Colorless powder
Melting point: 137–138° C.
$^1$H-NMR(DMSO-$d_6$)δ:
8.50(1H, d, J=6.6Hz), 7.30–7.50(9H, m), 6.10(1H, t, J=5.9Hz), 5.42(2H, s), 5.27(1H, t, J=4.95Hz, $D_2O$*1), 4.53(2H, s), 4.09–4.21(2H, m), 3.56–3.73(2H, m), 2.10–2.50(2H, m)

Compound 20

$R_1$ = H $R_2$ = 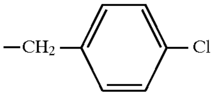

$R_3$ = 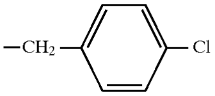

Yield: 62%
Crystal form: White needles
Melting point: 132–133° C.
$^1$H-NMR(DMSO-$d_6$)δ:
8.50(1H, d, J=5.28Hz), 7.30–7.60(8H, m), 6.10(1H, t), 5.41(2H, s), 5.27(1H, t, $D_2O$*1), 4.54(2H, s), 4.10–4.25(2H, m), 3.55–3.75(2H, m), 2.10–2.50(2H, m)

Compound 21

$R_1$ = H $R_2$ = 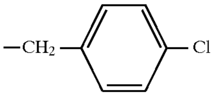

$R_3$ = 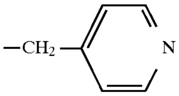

Yield: 31%
Crystal form: Colorless powder
Melting point: 144° C. (dec.)
$^1$H-NMR(DMSO-$d_6$)δ:
8.60(2H, d, J=5.93Hz), 8.54(1H, d, J=6.6Hz), 7.30–7.50(6H, m), 6.09(1H, t, J=5.78Hz), 5.49(2H, s), 5.29(1H, t, J=4.95Hz, $D_2O$*1), 4.54(2H, s), 4.10–4.21(2H, m), 3.55–3.75(2H, m), 2.10–2.50(2H, m)

Compound 22

$R_1$ = H $R_2$ = 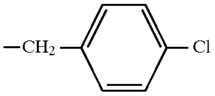

$R_3$ = $-CH_2CH_2N(CH_2CH_3)_2$
Yield: 20%
Crystal form: Colorless powder
Melting point: 104–106° C.
$^1$H-NMR(DMSO-$d_6$)δ:
8.45(1H, d, J=6.6Hz), 7.42(2H, d, J=8.6Hz), 7.37(2H, d, J=8.6Hz), 6.08(1H, t, J=5.9Hz), 5.25(1H, t, J=4.9Hz, $D_2O$*1), 4.53(2H, s), 4.38(2H, t, J=5.9Hz), 4.17–4.19(1H, m), 4.08–4.09 (1H, m), 3.62–3.65(2H, m), 2.76(2H, t, J=5.9Hz), 2.52(4H, q, J=7.3Hz), 2.47–2.50(1H, m), 2.13–2.45(1H, m), 0.95(6H, t, J=7.3Hz)

Compound 23

$R_1$ = H

TABLE 1-continued $R_2$ = 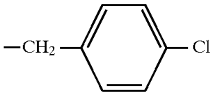

$R_3$ = 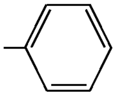

Yield: 22%
Crystal form: Colorless powder
Melting point: 169–171° C.
$^1$H-NMR(DMSO-$d_6$)δ:
8.64(1H, d, J=6.3Hz), 7.2–7.5(9H, m), 6.0–6.1(1H, m), 5.31 (1H, t, J=5.0Hz, $D_2O$*1), 4.53(2H, s), 4.17–4.21 (1H, m), 4.11–4.12(1H, m), 3.5–3.7(2H, m), 2.4–2.5(1H, m), 2.1–2.2(1H, m)

Compound 24

$R_1$ = H $R_2$ = 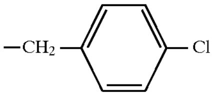

$R_3$ = $-CH(CH_3)_2$
Yield: 63%
Crystal form: White needles
Melting point: 161–163° C.
$^1$H-NMR(DMSO-$d_6$)δ:
8.44(1H, d, J=6.6Hz), 7.30–7.50(4H, m), 6.08(1H, t, J=6.43Hz), 5.20–5.40(2H, m, 1H分$D_2O$*1), 4.53(2H, s), 4.05–4.20(2H, m), 3.55–3.70(2H, m), 2.05–2.51(2H, m), 1.32(6H, d, J=6.3Hz), Compound 25

$R_1$ = H $R_2$ = 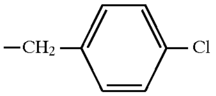

$R_3$ = $-CH_2CH_2OH$
Yield: 18%
Crystal form: Colorless powder
Melting point: 133–134° C.
$^1$H-NMR(DMSO-$d_6$)δ:
8.46(1H, d, J=6.6Hz), 7.43(2H, d, J=8.6Hz), 7.37(2H, d, J=8.6Hz), 6.08(1H, t, J=5.9Hz), 5.26(1H, t, J=5.0Hz, $D_2O$*1), 4.94(1H, t, J=5.6Hz, $D_2O$*1), 4.53(2H, s), 4.36(2H, t, J=4.6Hz), 4.17–4.19(1H, m), 4.09–4.10(1H, m), 3.60–3.74(4H, m), 2.40–2.49(1H, m), 2.08–2.18(1H, m)

Compound 26

$R_1$ = H $R_2$ = 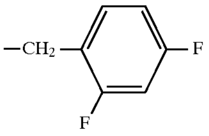

$R_3$ = $-CH_3$
Yield: 67%
Crystal form: Colorless powder
Melting point: 137–138° C.
$^1$H-NMR(DMSO-$d_6$)δ:
8.45(1H, d, J=6.6Hz), 7.07–7.57(3H, m), 6.07(1H, t, J=5.9Hz), 5.27(1H, t, J=4.9Hz, $D_2O$*1), 4.55(2H, s), 4.19–4.22(1H, m), 4.06–4.08(1H, m), 3.93(3H, s), 3.57–3.69 (2H, m), 2.39–2.47(1H, m), 2.09–2.19(1H, m)

TABLE 1-continued

Compound 27

$R_1$ = 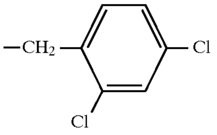

$R_2$ = H
$R_3$ = $-CH_2CH_3$
Yield: 61%
Crystal form: Colorless powder
Melting point: 119.5–120° C.
$^1$H-NMR(DMSO-$d_6$)δ:
8.15(1H, d, J=6.2Hz), 7.63(1H, d, J=2.0Hz), 7.55(1H, d, J=8.3Hz), 7.42(1H, dd, J=8.3Hz, 2.0Hz), 6.07(1H, t, J=6.2Hz), 5.35(1H, d, J=4.6Hz, $D_2O$*1), 4.61(2H, s), 4.37(2H, q, J=7.1Hz), 4.22–4.28(1H, m), 3.96–4.00(1H, m), 3.67–3.84 (2H, m), 2.10–2.31(2H, m), 1.32(3H, t, J=7.1Hz)

Compound 28

$R_1$ = H $R_2$ = 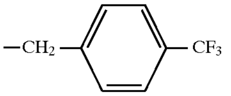

$R_3$ = $-CH_3$
Yield: 70%
Crystal form: Colorless powder
$^1$H-NMR(DMSO-$d_6$)δ:
8.46(1H, d, J=6.6Hz), 7.73(2H, d, J=8.0Hz), 7.57(2H, d, J=8.0Hz), 6.10(1H, t, J=5.8Hz), 5.26(1H, d, J=5.1Hz, $D_2O$*1), 4.65(2H, s), 4.11–4.23(2H, m), 3.93(3H, s), 3.59–3.69(2H, m), 2.44–2.50(1H, m), 2.10–2.20(1H, m)

Compound A $R_1$ = $-COCH_3$ $R_2$ = 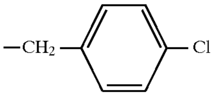

$R_3$ = $-CH_2CH_3$
Yield: 75%
Form: Thick syrup-like form
$^1$H-NMR(DMSO-$d_6$)δ:
8.16(1H, d, J=6.6Hz), 7.42(2H, d, J=8.5Hz), 7.38(2H, d, J=8.5Hz), 6.09(1H, t, J=6.6Hz), 4.54(2H, s), 4.40(2H, q, J=7.1Hz), 4.04–4.29(4H, m), 2.41–2.50(1H, m), 2.22–2.30(1H, m), 2.03(3H, s), 1.33(3H, t, J=7.1Hz)

Compound B $R_1$ = $-COCH_3$ $R_2$ = 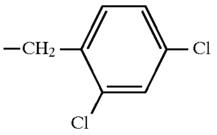

$R_3$ = $-CH_3$
Yield: 51%
Form: Thick syrup-like form
$^1$H-NMR(DMSO-$d_6$)δ:
8.18(1H, d, J=6.3Hz), 7.64(1H, d, J=2.0Hz), 7.55(1H, d, J=8.2Hz), 7.46(1H, dd, J=8.2Hz, J=2.0Hz), 6.12(1H, t, J=5.8Hz), 4.60(2H, s), 4.22–4.30(4H, m), 3.93(3H, s), 2.46–2.52(1H, m), 2.25–2.34(1H, m), 2.04(3H, s)

Compound C $R_1$ = $-COCH_3$

TABLE 1-continued

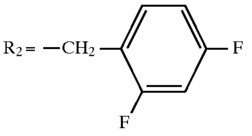

$R_3$ = $-CH_2CH_3$
Yield: 82%
Form: Thick syrup-like form
$^1$H-NMR(DMSO-$d_6$)δ:
8.17(1H, d, J=6.6Hz), 7.06–7.60(3H, m), 6.08(1H, t, J=6.6Hz), 4.56(2H, s), 4.40(2H, q, J=7.3Hz), 4.10–4.30(4H, m), 2.20–2.49(2H, m), 2.03(3H, s), 1.33(3H, t, J=7.3Hz)

Compound D $R_1$ = $-COCH_3$

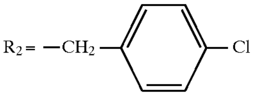

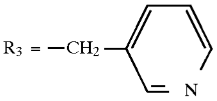

Yield: 50%
Crystal form: Colorless powder
$^1$H-NMR(DMSO-$d_6$)δ:
8.70(1H, d, J=1.7Hz), 8.59(1H, dd, J=1.7Hz, 4.6Hz), 8.22(1H, d, J=6.3Hz), 7.89–7.93(1H, m), 7.36–7.48(5H, m), 6.11(1H, t, J=6.1Hz), 5.48(2H, s), 4.55(2H, s), 4.19–4.30(4H, m), 2.44–2.52(1H, m), 2.22–2.32(1H, m), 2.03(3H, s)

Compound E $R_1$ = $-COCH_3$

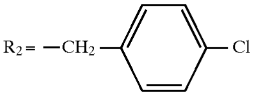

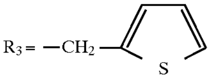

Yield: 42%
Form: Thick syrup-like form
$^1$H-NMR(DMSO-$d_6$)δ:
8.21(1H, d, J=6.6Hz), 7.60–7.63(1H, m), 7.25–7.65(5H, m), 7.04–7.08(1H, m), 6.11(1H, t, J=6.6Hz), 5.62(2H, s), 4.54(2H, s), 4.15–4.50(4H, m), 2.45–2.50(1H, m), 2.20–2.33(1H, m), 2.03(3H, s)

Compound F $R_1$ = $-COCH_3$

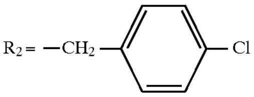

$R_3$ = $-CH_2CH_2OCOCH_3$
Yield: 81%
Form: Thick syrup-like form
$^1$H-NMR(DMSO-$d_6$)δ:
8.20(1H, d, J=6.6Hz),7.43(2H, d, J=8.9Hz), 7.38(2H, d, J=8.9Hz), 6.09(1H, t, J=6.6Hz), 4.54(2H, s), 4.20–4.37(4H, m), 3.98–4.03 (2H, m), 3.50–3.60(2H, m), 2.40–2.50(1H, m), 2.05–2.30(1H, m), 2.04(3H, s), 2.01(3H, s)

Compound G $R_1$ = $-COCH_3$

TABLE 1-continued

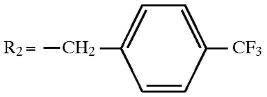

$R_3$ = $-CH_3$
Yield: 74%
Form: Thick syprup-like form
$^1$H-NMR(DMSO-$d_6$)δ:
8.18(1H, d, J=6.3Hz), 7.73(2H, d, J=8.0Hz), 7.58(2H, d, J=8.0Hz), 6.12(1H, t, J=5.9Hz), 4.66(2H, s), 4.20–4.30(4H, m), 3.94(3H, s), 2.20–2.54(2H, m), 2.03(3H, s)

Compound H

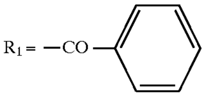

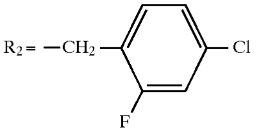

$R_3$ = $-CH_2CH_3$
Yield: 81%
Form: Thick syrup-like form
$^1$H-NMR(DMSO-$d_6$)δ:
8.16(1H, d, J=6.3Hz), 7.93(2H, d, J=6.3Hz), 7.25–7.72(6H, m), 6.11(1H, t, J=6.3Hz), 4.63(2H, s), 4.50–4.58(2H, m), 4.31–4.45 (4H, m), 2.30–2.50(2H, m), 1.32(3H, t, J=7.3Hz)

Compound I

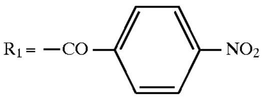

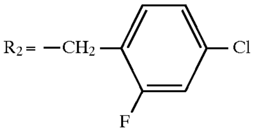

$R_3$ = $-CH_2CH_3$
Yield: 66%
Crystal form: Colorless powder
Melting point: 116–117° C.
$^1$H-NMR(DMSO-$d_6$)δ:
8.35(2H, d, J=8.9Hz), 8.19(1H, d, J=6.6Hz), 8.17(2H, d, J=8.9Hz), 7.25–7.55(3H, m), 6.12(1H, t, J=6.6Hz), 4.57–4.66(4H, m), 4.34–4.44(4H, m), 2.30–2.49(2H, m), 1.32(3H, t, J=6.9Hz)

Compound J

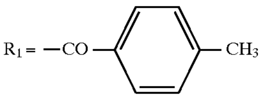

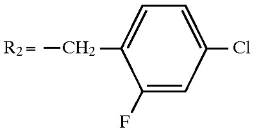

$R_3$ = $-CH_2CH_3$
Yield: 82%
Form: Thick syrup-like form

TABLE 1-continued $^1$H-NMR(DMSO-$d_6$)δ:
8.15(1H, d, J=6.6Hz), 7.81(2H, d, J=7.9Hz), 7.25–7.55(5H, m),
6.09(1H, t, J=6.6Hz), 4.62(2H, s), 4.48–4.54(2H, m),
4.31–4.43(4H, m), 2.25–2.58(5H, m), 1.32(3H, t, J=7.3Hz)

*1: The peak disappeared by addition of $D_2O$.

REFERENCE EXAMPLE 1

Synthesis of 3'-O-(4-chloro-2-fluorobenzyl)-2'-deoxy-5-fluorouridine (comparative compound 1)

The title compound was prepared according to the process disclosed in Japanese Unexamined Patent Publication No. 106593/1986. The process was carried out as follows. A 5.0 g quantity of 2'-deoxy-5'-O-trityl-5-fluorouridine was dissolved in 40 ml of tetrahydrofuran. To the solution was added 856 mg of 60% sodium hydride, followed by 1 hour of stirring at room temperature. After addition of 2.58 g of 4-chloro-2-fluorobenzyl bromide, the mixture was stirred at room temperature for 2 hours. The reaction mixture was cooled to 0° C. and saturated ammonium chloride was added in excess. The tetrahydrofuran layer was washed with a saturated aqueous solution of sodium chloride and dried over magnesium sulfate. The solvent was distilled off at reduced pressure, and the residue was purified by silica gel column chromatography (eluate: n-hexane-ethyl acetate (3:2)), giving 5.03 g of the title compound (yield 78%).

Melting point: 154°–155° C.

$^1$H-NMR (DMSO-$d_6$) δ: 11.85 (1H, s, *1) 8.20 (1H, d, J=7.3 Hz), 7.51 (1H, t, J=8.2 Hz), 7.45 (1H, dd, J=9.9 Hz, 2.0 Hz), 7.32 (1H, dd, J=8.2 Hz, 2.0 Hz), 6.11 (1H, t, J=5.9 Hz), 5.24 (1H, t, J=4.9 Hz, *1), 4,57 (2H, s), 4.21 (1H, m), 4.02–4.03 (1H, m), 2.12–2.38 (2H, m) (*1=The peak disappeared by addition of $D_2O$)

REFERENCE EXAMPLE 2

Synthesis of 2'-deoxy-4-O-n-propyl-5-fluorouridine (comparative compound 2)

A 8.25 g quantity of 3',5'-O-diacetyl-2'-deoxy-5-fluorouridine was dissolved in 120 ml of acetonitrile. To the solution was added 20.5 g of 1-methylimidazole. With ice-cooling, 11.5 g of phosphorus oxychloride was added and the mixture was warmed to room temperature, followed by 1.5 hours of stirring. After addition of 12.6 ml of triethylamine and 15 g of n-propanol, the mixture was stirred at room temperature for 2 hours. The precipitated solids were removed by filtration and the mother liquor was concentrated at reduced pressure. To the residue was added ethyl acetate and the mixture was washed with water and dried over magnesium sulfate. The solvent was distilled off and the residue was dissolved in 30 ml of n-propanol. To the solution was added an alcoholate solution of 150 ml of metal sodium in 20 ml of n-propanol. The mixture was stirred at room temperature for 30 minutes. The reaction mixture was neutralized with a strongly acidic ion exchange resin (Dowex 50W, H$^+$ form, product of Dow Chemical Co.). The resin was filtered off and the filtrate was concentrated. The residue was purified by silica gel column chromatography (eluate: chloroform-methanol (10:1)), giving 24.6 g of the title compound (yield 64%).

$^1$H-NMR (DMSO-$d_6$) δ: 8.49 (1H, d, J=6.6 Hz), 6.06 (1H, t, J=6.1 Hz), 5.25 (1H, d, J=4.3 Hz, *1), 5.19 (1H, t, J=5.0 Hz, *1), 4.20–4.32 (3H, m), 3.81–3.85 (1H, m), 3.54–3.70 (2H, m), 2.20–2.28 (1H, m), 1.99–2.10 (1H, m), 1.67–1.80 (2H, m), 0.94 (3H, t, J=5.4 Hz) (*1=The peak disappeared by addition of $D_2O$ )

Pharmacological Test Example 1

The compounds of the present invention were tested for antitumor effect. The results are shown below.
Test Method Rat-transplantable tumor, Yoshida sarcoma cells ($2\times10^4$) were subcutaneously transplanted in the back of male Donryu/CRJ strain rats (weighing 150 to 165 g). The test compounds were suspended in a 0.5% aqueous solution of hydroxypropylmethyl cellulose. Twenty-four hours after the transplantation, each suspension was orally administered to rats (7 rats in each group) in an amount of 1.0 ml per 100 g of rats' body weight once a day for 7 consecutive days. Only a solution of hydroxypropylmethyl cellulose containing no test compound was orally administered to the control group in an amount of 1.0 ml/100 g rats' body weight once a day for 7 consecutive days starting 24 hours after the transplantation.

The rats were sacrificed on the 8th day after the transplantation and their tumors were extirpated. The tumors were weighed to calculate an average tumor weight at each dose. The results were compared between the treated group and the control group. An effective dose ($ED_{50}$) for achieving 50% inhibition of tumor growth was determined from the dose-tumor reduction curve. A dose of 50% inhibition of body weight gain ($BWC_{50}$) was determined from the dose-body weight change curve. The therapeutic index (T.I.= $BWC_{50}/ED_{50}$) was also determined. The results are shown below in Table 2.

TABLE 2

| Test Compound | $ED_{50}$ (mg/kg/day) | $BWC_{50}$ (mg/kg/day) | T.I. |
| --- | --- | --- | --- |
| Compound 3 | 4 | 14 | 3.5 |
| Compound 7 | 7.5 | 18 | 2.4 |
| Compound 12 | 3 | 16 | 5.3 |
| Comparative Compound 1 | 7.5 | 8.5 | 1.1 |
| Comparative Compound 2 | 34 | 37 | 1.1 |
| Comparative Compound 3 | >40 | 40 | <1.0 |
| FdUrd (CVI) | 0.8 | 0.7 | 0.88 |
| FdUrd (iv) | 44 | 60 | 1.36 |

Comparative Compound 1: 3'-O-(4-chloro-2-fluorobenzyl)-2'-deoxy-5-fluorouridine
Comparative Compound 2: 2'-deoxy-4-O-n-propyl-5-fluorouridine
Comparative Compound 3: 2'-deoxy-4-O-(4-fluorobenzyl)-3',5'-di-O-n-pentanoyl-5-fluorouridine (compound disclosed in Japanese Unexamined Patent Publication No. 109722/1982)

FdUrd (CVI): 2'-deoxy-5-fluorouridine administered by continuous intravenous drip injection FdUrd (iv): 2'-deoxy-5-fluorouridine administered by intravenous injection Table 2 shows that the compounds of the present invention are higher in efficacy and greater in therapeutic index than conventional compounds, i.e. 3'-O-(4-chloro-2-fluorobenzyl)-2'-deoxy-5-fluorouridine, 2'-deoxy-4-O-n-propyl-5-fluorouridine,2'-deoxy-4-O-(4-fluorobenzyl)-3',5'-di-O-n-pentanoyl-5-fluorouridine and 2'-deoxy-5-fluorouridine, hence superior in anti-cancer effect.

Pharmacological Test Example 2

Test Method (a) A tumor piece (about 2 $mm^3$) of nude rat-transplantable human kidney cancer strain, JRC-11, was subcutaneously transplanted in the armpit of each male F344/N Jcl-rnu nude rat. The treatment of rats (7 rats in each group) started when the rats' tumors grew to an estimated volume of 250 $mm^3$ as calculated by an equation $$V=1/2L\times W^2$$

wherein L is the length of the tumor and W is the width of the tumor, each being measured by calipers. The treated group (rats to be treated with the test compounds) and the control group were tested under equal conditions concerning the mean value of tumor volume and standard deviation. The test compounds were suspended in a 0.5% aqueous solution of hydroxypropylmethyl cellulose. Each suspension was orally administered to rats in an amount of 1.0 ml per 100 g of rats' body weight once a day for 14 consecutive days. Only a solution of hydroxypropylmethyl cellulose containing no test compound was orally administered to the control group in an amount of 1.0 ml per 100 g rats' body weight once a day for 14 consecutive days.

A ratio of tumor growth of each rat was calculated from two tumor volumes on the first day of administration and on the day following the last administration. A mean ratio of tumor growth of the group (T) or the control group (C) was calculated from said ratio. Then, a tumor growth inhibition ratio (%) was calculated by the following equation:

$$\text{Inhibition ratio (\%)}=(1-T/C)\times 100$$

wherein T/C is the mean ratio of tumor growth of the group (T)/that of the control group (C). The results are shown below in Table 3.

(b) The same experiment as in (a) was conducted except that a nude rat-transplantable human stomach cancer strain, H-81, was used in place of the nude rat-transplantable human kidney cancer strain, JRC-11. A tumor growth inhibition ratio was calculated. The results are also shown in Table 3.

TABLE 3

| Test Compound | Dose (mg/kg) | Strain | Inhibition ratio (%) |
|---|---|---|---|
| Compound 13 | 3.75 | H-81 | 74 |
| | 7.5 | H-81 | 79 |
| Compound 13 | 3.75 | JRC-11 | 67 |
| | 7.5 | JRC-11 | 73 |

In the above experiments, the rats were visually checked for the change of body. The rats showed substantially no reduction in the body weight and no rat died.

Preparation Examples are given below to illustrate the production of pharmaceutical preparations using the compounds of the present invention.

PREPARATION EXAMPLE 1

(Capsules)

Capsules were produced in the conventional manner according to the following composition:

| | |
|---|---|
| Compound 3 | 200 mg |
| Lactose | 30 mg |
| Corn starch | 50 mg |
| Crystalline cellulose | 10 mg |
| Magnesium stearate | 3 mg |
| Total (per capsule) | 293 mg |

PREPARATION EXAMPLE 2

(Tablets)

Tablets were produced in the conventional manner according to the following composition:

| | |
|---|---|
| Compound 7 | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty acid glyceride | 2 mg |
| Titanium dioxide | 2 mg |
| Total (per tablet) | 300 mg |

PREPARATION EXAMPLE 3

(Granules)

Granules were produced in the conventional manner according to the following composition:

| | |
|---|---|
| Compound 12 | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Total (per wrapper) | 1000 mg |

PREPARATION EXAMPLE 4

(Fine granules)

Fine granules were produced in the conventional manner according to the following composition:

| | |
|---|---|
| Compound 13 | 200 mg |
| Mannitol | 520 mg |
| Corn starch | 100 mg |
| Crystalline cellulose | 100 mg |
| Hydroxypropyl cellulose | 70 mg |
| Talc | 10 mg |
| Total (per wrapper) | 1000 mg |

PREPARATION EXAMPLE 5

(Injection)

An injection solution was produced in the conventional manner according to the following composition

:

| | |
|---|---|
| Compound 22 | 100 mg |
| Distilled water for injections | q.s. |
| Total (per vial) | 2 ml |

PREPARATION EXAMPLE 6

(Suppositories)

Suppositories were produced in the conventional manner according to the following composition:

| | |
|---|---|
| Compound 27 | 200 mg |
| Witepsol S-55 | 1300 mg |
| (Mixture of mono-, di- and tri-glycerides of saturated fatty acids such as lauric acid and stearic acid, product of Dynamite Nobel Co., Ltd.) | |
| Total (per piece) | 1500 mg |

What we claim is:

1. A 2'-deoxy-5-fluorouridine derivative represented by the formula

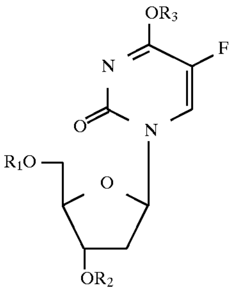

wherein $R_1$ is a hydrogen atom or a group easily hydrolyzable in vivo, $R_2$ is a benzyl group having at least one halogen atom as a substituent on the phenyl ring, and $R_3$ is a lower alkyl group, or a pharmaceutically acceptable salt thereof.

2. A 2'-deoxy-5-fluorouridine derivative according to claim 1 wherein $R_1$ is a hydrogen atom or an easily hydrolyzable group in vivo selected from the group consisting of a lower alkanoyl group or an arylcarbonyl group and $R_2$ is a benzyl group having at least one halogen atom as a substituent on the phenyl ring, or a pharmaceutically acceptable salt thereof.

3. A 2'-deoxy-5-fluorouridine derivative according to claim 1 wherein $R_1$ is a hydrogen atom or an easily hydrolyzable group in vivo selected from the group consisting of an acetyl group, a benzoyl group, a 4-methylbenzoyl group or a 4-nitrobenzoyl group, $R_2$ is a benzyl group having one or two halogen atoms as substituents on the phenyl ring and $R_3$ is a lower alkyl group, or a pharmaceutically acceptable salt thereof.

4. A 2'-deoxy-5-fluorouridine derivative according to claim 1 wherein $R_1$ is a hydrogen atom, $R_2$ is a benzyl group which has one or two halogen atoms as substituents on the phenyl ring, and $R_3$ is a lower alkyl group, or a pharmaceutically acceptable salt thereof.

5. A process for preparing the 2'-deoxy-5-fluorouridine derivative of the formula (I) as defined in claim 1, the process comprising the steps of reacting a compound represented by the formula (II)

(II)

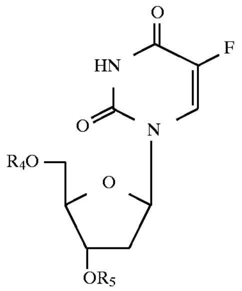

wherein one of $R_4$ and $R_5$ is a benzyl group which may optionally have at least one halogen atom as a substituent on the phenyl ring, and the other is an acyl group, with a halogenating agent in the presence of a base; further adding a base to the resulting reaction mixture; reacting the mixture with an alcohol represented by the formula $R_3'OH$ wherein $R_3'$ is a benzyl group which may optionally have at least one halogen atom as a substituent on the phenyl ring, a phenyl group, a lower alkenyl group or a lower alkyl group optionally having at least one substituent selected from the group consisting of a hydroxyl group, a lower alkoxy group, a di-lower alkylamino group, a furanyl group, a thienyl group, a pyridyl group and a lower alkanoyl group to produce a compound represented by the formula (I-a)

(I-a)

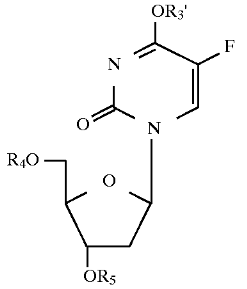

wherein $R_3'$, $R_4$ and $R_5$ are as defined above; subjecting the compound of the formula (I-a) to a reaction for the removal of acyl group in the presence of a base to give a compound represented by the formula (I-b)

(I-b)

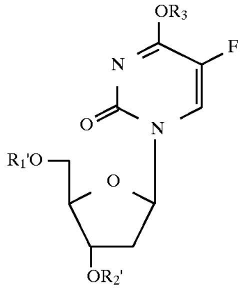

wherein one of $R_1'$ and $R_2'$ is a benzyl group which may optionally have at least one halogen atom or trifluoromethyl group as a substituent on the phenyl ring, the other is a hydrogen atom, and $R_3$ is as defined above; and optionally converting the group of $R_1'$ or $R_2'$ to a group easily hydrolyzable in vivo.

6. An antitumor composition comprising an effective amount of the 2'-deoxy-5-fluorouridine derivative as defined in claim 1 or a pharmaceutically acceptable salt thereof and a pharmaceutically acceptable carrier.

7. An antitumor composition comprising an effective amount of the 2'-deoxy-5-fluorouridine derivative as defined in claim 1 wherein $R_1$ is a hydrogen atom, $R_2$ is a benzyl group having one or two halogen atoms as substituents on the phenyl ring and $R_3$ is a lower alkyl group or a pharmaceutically acceptable salt thereof and a pharmaceutically acceptable carrier.

8. A method of treating mammals' tumors, comprising administering to a mammal the 2'-deoxy-5-fluorouridine derivative as defined in claim 1 or a pharmaceutically acceptable salt thereof.

9. A method of treating mammals' tumors, comprising administering to a mammal the 2'-deoxy-5-fluorouridine derivative as defined in claim 1 wherein $R_1$ is a hydrogen atom, $R_2$ is a benzyl group having one or two halogen atoms as substituents on the phenyl ring and $R_3$ is a lower alkyl group, or a pharmaceutically acceptable salt thereof.

* * * * *